United States Patent
Li et al.

(10) Patent No.: US 9,634,260 B2
(45) Date of Patent: Apr. 25, 2017

(54) METHOD FOR PREPARING CONJUGATED COMPOUND HAVING PHENOXATHIIN AND ELECTRON DONATING GROUP OF CONJUGATED AROMATIC UNIT, AND OLED DEVICE HAVING THE CONJUGATED COMPOUND

(71) Applicant: Shenzhen China Star Optoelectronics Technology Co., Ltd., Shenzhen (CN)

(72) Inventors: Xianjie Li, Shenzhen (CN); Yuanchun Wu, Shenzhen (CN); Shijian Su, Shenzhen (CN); Ming Liu, Shenzhen (CN); Kunkun Liu, Shenzhen (CN)

(73) Assignee: SHENZHEN CHINA STAR OPTOELECTRONICS TECHNOLOGY CO., LTD., Shenzhen, Guangdong (CN)

( * ) Notice: Subject to any disclaimer, the term of this patent is extended or adjusted under 35 U.S.C. 154(b) by 0 days.

(21) Appl. No.: 14/763,827

(22) PCT Filed: May 22, 2015

(86) PCT No.: PCT/CN2015/079538
§ 371 (c)(1),
(2) Date: Jul. 28, 2015

(87) PCT Pub. No.: WO2016/173019
PCT Pub. Date: Nov. 3, 2016

(65) Prior Publication Data
US 2016/0322584 A1  Nov. 3, 2016

(30) Foreign Application Priority Data
Apr. 29, 2015 (CN) .......................... 2015 1 0213031

(51) Int. Cl.
*H01L 29/08* (2006.01)
*H01L 51/00* (2006.01)
(Continued)

(52) U.S. Cl.
CPC ........ *H01L 51/0071* (2013.01); *C07D 411/04* (2013.01); *C07D 411/14* (2013.01);
(Continued)

(58) Field of Classification Search
USPC .......................................................... 257/40
See application file for complete search history.

(56) References Cited

U.S. PATENT DOCUMENTS 3,882,231 A * 5/1975 Fleming ............... A61K 31/535
                                                  514/217.03
4,031,147 A * 6/1977 Graham ................ B01J 31/0218
                                                  502/168
(Continued)

FOREIGN PATENT DOCUMENTS

WO    WO2014030822 A1    2/2014

*Primary Examiner* — Caleb Henry
(74) *Attorney, Agent, or Firm* — Leong C. Lei

(57) ABSTRACT

The disclosure provides a conjugated compound having phenoxathiinl, method for preparing the same and OLED. The conjugated compound has one of the following formulas:

Formula 1

(Continued)

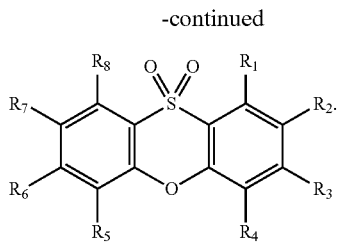

Formula 2

Different kinds of electron-rich conjugated aromatic units are reacted with intermediate having phenoxathiinl by Suzuki coupling, Buchwald-Hartwig coupling, or Cu-catalyzed amination of halogenated aromatic hydrocarbons for forming the conjugated compound having phenoxathiin. The prepared novel compound is fluorescent, so that it can be used as the material of light emitting layer of OLED devices.

9 Claims, 3 Drawing Sheets

(51) Int. Cl.
| | |
|---|---|
| C09K 11/06 | (2006.01) |
| C07D 411/04 | (2006.01) |
| C07D 411/14 | (2006.01) |
| C07D 417/04 | (2006.01) |
| C07D 417/14 | (2006.01) |
| H01L 51/50 | (2006.01) |

(52) U.S. Cl.
CPC ......... *C07D 417/04* (2013.01); *C07D 417/14* (2013.01); *C09K 11/06* (2013.01); *H01L 51/005* (2013.01); *H01L 51/006* (2013.01); *H01L 51/0061* (2013.01); *H01L 51/0072* (2013.01); *C09K 2211/1007* (2013.01); *C09K 2211/1025* (2013.01); *C09K 2211/1029* (2013.01); *C09K 2211/1037* (2013.01); *H01L 51/0058* (2013.01); *H01L 51/5012* (2013.01)

(56) References Cited

U.S. PATENT DOCUMENTS

| | | | | |
|---|---|---|---|---|
| 4,069,263 | A * | 1/1978 | Lin | C07C 17/12 502/168 |
| 4,069,264 | A * | 1/1978 | Lin | C07C 17/12 502/168 |
| 4,190,609 | A * | 2/1980 | Lin | C07C 17/12 502/161 |
| 4,289,916 | A * | 9/1981 | Nakayama | C07C 17/12 502/168 |
| 4,647,709 | A * | 3/1987 | Wolfram | C07C 17/12 570/209 |
| 5,036,067 | A * | 7/1991 | Girard | C07D 279/18 514/211.11 |
| 5,077,374 | A * | 12/1991 | Cleary | C08G 75/0231 528/388 |
| 5,095,157 | A * | 3/1992 | Mais | C07C 201/12 568/937 |
| 6,930,216 | B2 * | 8/2005 | Mack | C07C 17/12 570/208 |
| 2005/0176969 | A1 * | 8/2005 | Herlihy | C07D 279/20 549/3 |
| 2006/0199943 | A1 * | 9/2006 | Falcou | C08G 61/02 528/422 |
| 2010/0221646 | A1 * | 9/2010 | Kawamonzen | G03H 1/02 430/2 |
| 2012/0003274 | A1 * | 1/2012 | Brand | C07D 327/08 424/400 |
| 2012/0003303 | A1 * | 1/2012 | Brand | A61K 9/2846 424/451 |
| 2012/0085997 | A1 | 4/2012 | Sugita | |
| 2013/0200360 | A1 * | 8/2013 | Oikawa | B82Y 20/00 257/40 |
| 2014/0203269 | A1 * | 7/2014 | Tada | C09K 11/06 257/40 |

* cited by examiner

METHOD FOR PREPARING CONJUGATED COMPOUND HAVING PHENOXATHIIN AND ELECTRON DONATING GROUP OF CONJUGATED AROMATIC UNIT, AND OLED DEVICE HAVING THE CONJUGATED COMPOUND

TECHNICAL FIELD

The disclosure is related to the field of light-emitting materials, and more particularly to a conjugated compound having phenoxathiinl, a method for preparing the same and an OLED device.

RELATED ART

Organic light-emitting diodes (OLED) have been widely used for the reasons of high efficiencies, being driven by a low voltage, being easily manufactured with a great area and displaying with full color. The studies began from 1950s. Dr. Ching W. Tang et. al. in Kodak (US) published a sandwich structure device in U.S. Pat. No. 4,356,429. When the OLED device is driven by a 10V DC current, the luminous intensity can reach the level of 1000 cd/m2, which is an important milestone. In the past twenty years, OLED using new emitters, especially organo-heavy metal complex phosphorescence emitters, have achieved significant success. However, it is difficult to obtain phosphors having suitable band gaps. Currently, the amount of blue phosphors with high efficiency (yCIE<0.15, yCIE+xCIE<0.30) is rare. In addition, as compared with green phosphors and red phosphors, it is challenging to obtain blue phosphors having a high energy level of triplet state. Further, the lifespan of blue phosphors is unstable, which limits the real application. Thus, it is important to develop stable blue phosphors with high efficiency. Based on many factors, the cost can be lowered and the process can be simplified for OLED full color displaying or white illuminating by using blue phosphors. Conventional blue phosphors can be categorized into n-type molecule and p-type molecule. The performance of the phosphors is mainly determined by electrons or holes, such that is it difficult to balance the carries, and the current efficiency and quantum efficiency of the devices are low. Simple designs of Donor-Acceptor (D-A) molecules can achieve bipolar transfer, such that balancing the carries can be achieved. However, the band gap is narrower because of the intramolecular charge transfer between the donor unit and the acceptor unit, so that the peak is red-shift, and ideal blue light cannot be obtained. To overcome the difficulty, a donor having an appropriate electron-donating ability and an acceptor having an appropriate electron-withdrawing ability should be combined as a molecule, such that the intramolecular charge transfer can be controlled in a certain level. Thereby, blue organic fluorescent materials with better performance and higher color purity can be obtained.

At present, most of the skeleton of the deposited molecule used in OLED is sulfur dibenzofuran, phosphorous oxide, triphenylamin and so forth. However, the organic light emitting small molecule having phenoxathiinl is rarely reported.

The OLED have been well developed. White devices having simple structure and high efficiency can be obtained by hybridization of fluorescence and phosphorescence. The devices obtained by hybridization of fluorescence and phosphorescence rely on the fluorescence efficiency. Thus, it is important to synthesize fluorescence materials having better efficiencies. Therefore, the inventors developed a series of fluorescence materials, which have novel structures and are easily synthesized.

SUMMARY

One purpose of the disclosure is to provide a conjugated compound having phenoxathiinl. The compound is a small molecule, the compound has a single structure, the molecular weight of the compound can be precisely measured, the compound is fluorescent, and the solubility and filming of the compound is good, so that the compound can be served as the material of the light emitting layer of the organic light-emitting diode.

Another purpose of the disclosure is to provide a method for preparing the conjugated compound having phenoxathiin. The method can be handled easily, the purification process is simple, and the yield of the target product is high.

Another purpose of the disclosure is to provide an organic light-emitting diode device. The conjugated compound having phenoxathiin is applied as the material of light emitting layer of the organic light-emitting devices, such as organic light-emitting diode devices, so that the luminous efficiency and stability are improved.

In order to achieve the above purposes, the disclosure provides a conjugated compound having phenoxathiin, wherein the conjugated compound has one of the following formulas:

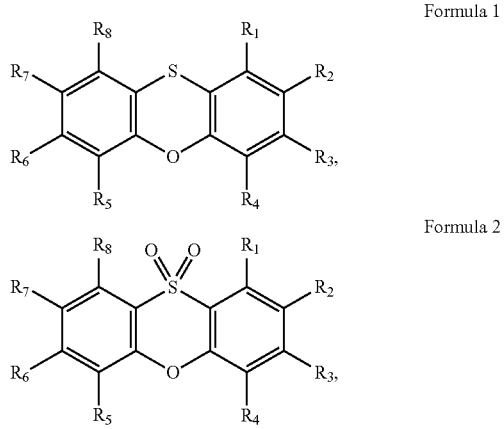

Formula 1

Formula 2 in the Formula 1 and the Formula 2, at least one of $R_1$-$R_8$ is an electron donating group of conjugated aromatic unit, alkyl-substituted aromatic unit, alkoxyl-substituted aromatic unit, alkyl- and alkoxyl-substituted aromatic unit, the aromatic unit is selected from one or more from the group constituted of an aromatic ring formed by vinylene group, ethynylene group, C and H atoms, an aromatic heterocyclic group formed by C, N and H atoms, an aromatic heterocyclic group formed by C, N, O and H atoms, an aromatic heterocyclic group formed by C, S and H atoms, and an aromatic heterocyclic group formed by C, Si and H atoms.

The disclosure also provides a method for preparing the conjugated compound having phenoxathiin according to claim 1, wherein the method comprises: first, preparing an intermediate having phenoxathiin, and then reacting the intermediate having phenoxathiin with a compound having an electron-rich conjugated aromatic unit by Suzuki coupling, Buchwald-Hartwig coupling, or Cu-catalyzed amination of halogenated aromatic hydrocarbons for forming the conjugated compound having phenoxathiin.

The intermediate having phenoxathiin is compound M1, M2, M3 or M4, and the structural formulas of M1, M2, M3 or M4 are:

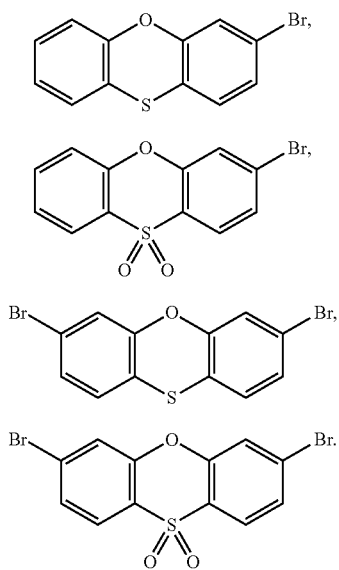

The method and the reactions for preparing the intermediate having phenoxathiin of M1 and M2 are:

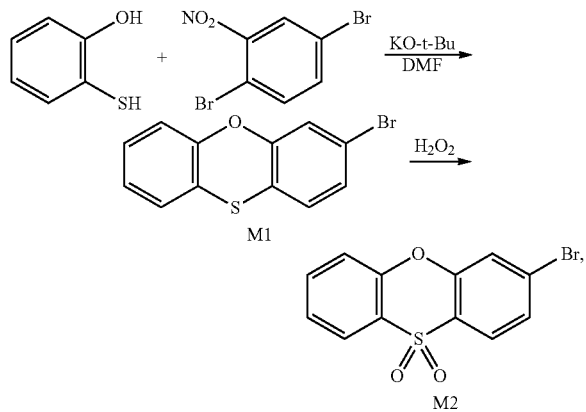

the method for preparing the intermediate having phenoxathiin of M1 is:

3 g of 2-hydroxy-benzenethiol and 120 mL of anhydrous N,N-dimethyl formamide being incorporated into a 250 mL three-necked flask and being stirred under Ar, with the protection of air, 5.47 g of potassium tert-butoxide being incorporated, after stirring for 0.5 hour, 7.01 g of 2,5-dibromo nitrobenzene being slowly incorporated, after stirring for 20 minutes, being heated under reflux overnight, after most of the anhydrous N,N-dimethyl formamide being vaporized by a rotary concentrator, the product being extracted by deionized water and dichloromethane and being separated by silica gel chromatography for obtaining a white solid of the intermediate of M1;

the method for preparing the intermediate having phenoxathiin of M2 is:

4.2 g of M1 and 50 mL of glacial acetic acid being incorporated into a 100 mL three-necked flask, after stirring, 10 mL of 30% hydrogen peroxide being incorporated, then, being heated under reflux overnight, after cooling, alcohol being incorporated, then, being vacuum filtrated, after drying, a white solid of the intermediate of M2 being obtained.

The method and the reactions for preparing the intermediate having phenoxathiin of M3 and M4 are:

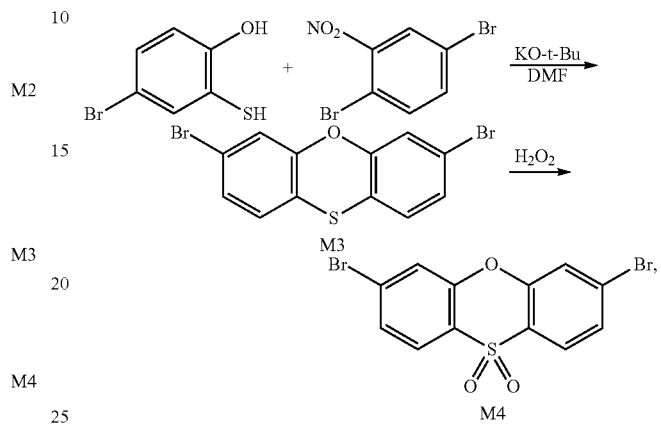

the method for preparing the intermediate having phenoxathiin of M3 is:

5 g of 5-bromo-2-hydroxy-benzenethiol and 120 mL of anhydrous N,N-dimethyl formamide being incorporated into a 250 mL three-necked flask and being stirred under Ar, with the protection of air, 5.47 g of potassium tert-butoxide being slowly incorporated, after stirring for 0.5 hour, 7.01 g of 2,5-dibromo nitrobenzne being incorporated, after stirring for 20 minutes, being heated under reflux overnight, after most of the anhydrous N,N-dimethyl formamide being vaporized by a rotary concentrator, being extracted by deionized water and dichloromethane and being separated by silica gel chromatography for obtaining a white solid of the intermediate of M3; and the method for preparing the intermediate having phenoxathiin of M4 is:

4.6 g of the intermediate of M3 and 50 mL of glacial acetic acid being incorporated into a 100 mL three-necked flask, after stirring, 10 mL of 30% hydrogen peroxide being incorporated, being heated under reflux overnight, after cooling, alcohol being incorporated, being vacuum filtrated, after drying, a white solid of the intermediate of M4 being obtained.

The electron-rich conjugated aromatic unit is N,N-dimethyl vinyl urea, 9,10-dihydro-9,9-dimethyl-acridine, N,N-diphenyl-4-(4,4,5,5-tetramethyl-1,3,2-dioxa pentaborane-2-yl) aniline, bis-(4-tert-butylphenyl) amine, phenothiazine, 9-phenyl-3-(4,4,5,5-tetramethyl-1,3,2-dioxa pentaborane 2-yl) carbazole, phenoxazine or N,N-dimethyl vinyl urea.

The disclosure further provides an organic light-emitting diode device, comprising a substrate, an anode, a hole injection layer, a hole transfer layer, a light emitting layer, an electron transfer layer and a cathode disposed in sequence from the bottom to the top, characterized by, the light emitting layer including the conjugated compound having phenoxathiin according to claim 1.

The light emitting layer is formed by vacuum vapor deposition or solution coating.

The substrate is a glass substrate, the material of the anode is indium tin oxide, the cathode is a bilayer composite structure constituted by a LiF layer and an Al layer.

The material of the hole injection layer is HAT-CN, the material of the hole transfer layer is NPB and TCTA, the material of the electron transfer layer is TPBI, the structural formulas of HAT-CN, NPB, TCTA and TPBI are:

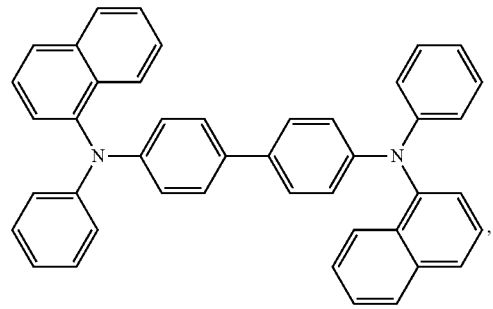

NPB

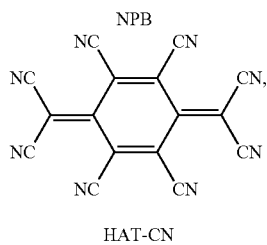

HAT-CN

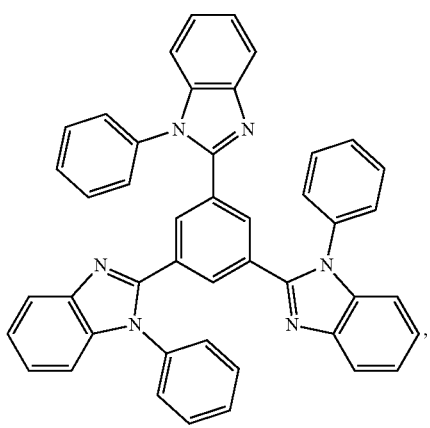

TPBi

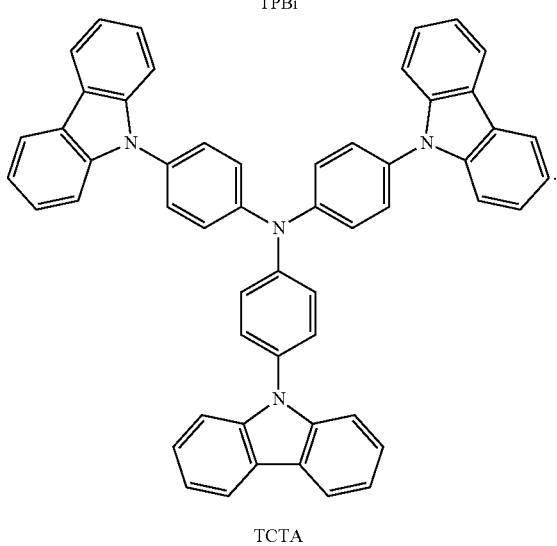

TCTA

As compared with present material and technologies, the disclosure has the following advantages and benefits:

(1) The conjugated compound having phenoxathiinl of the disclosure has a single structure, the molecular weight of the compound can be precisely measured, the compound can be easily purified, the reproducibility is good, and it is convenient to study the relationship between the structure and the properties of the compound;

(2) The conjugated compound having phenoxathiinl is a small molecule, so that it has a lower sublimation temperature and a lower deposition temperature, and the film patterns are more stable;

(3) The conjugated length and the illuminated color of the compound can be efficiently controlled by changing the chemical structure of the substituent at the phenoxathiinl;

(4) The physical properties of the compound and the properties of photoelectric device thereof can be improved by changing the substituent at the aromatic structure;

(5) The electron withdrawing ability of the phenoxathiinl can be adjusted by changing the valence state of sulfur atom in the phenoxathiinl, such that intramolecular charge transfer, energy level of the molecule and the transmission performance of carriers can be efficiently adjusted.

BRIEF DESCRIPTION OF THE DRAWINGS

In order to more clearly illustrate the embodiments of the disclosure, the accompanying drawings for illustrating the technical solutions and the technical solutions of the disclosure are briefly described as below.

In the drawings.

DETAILED DESCRIPTION

Figure 1:
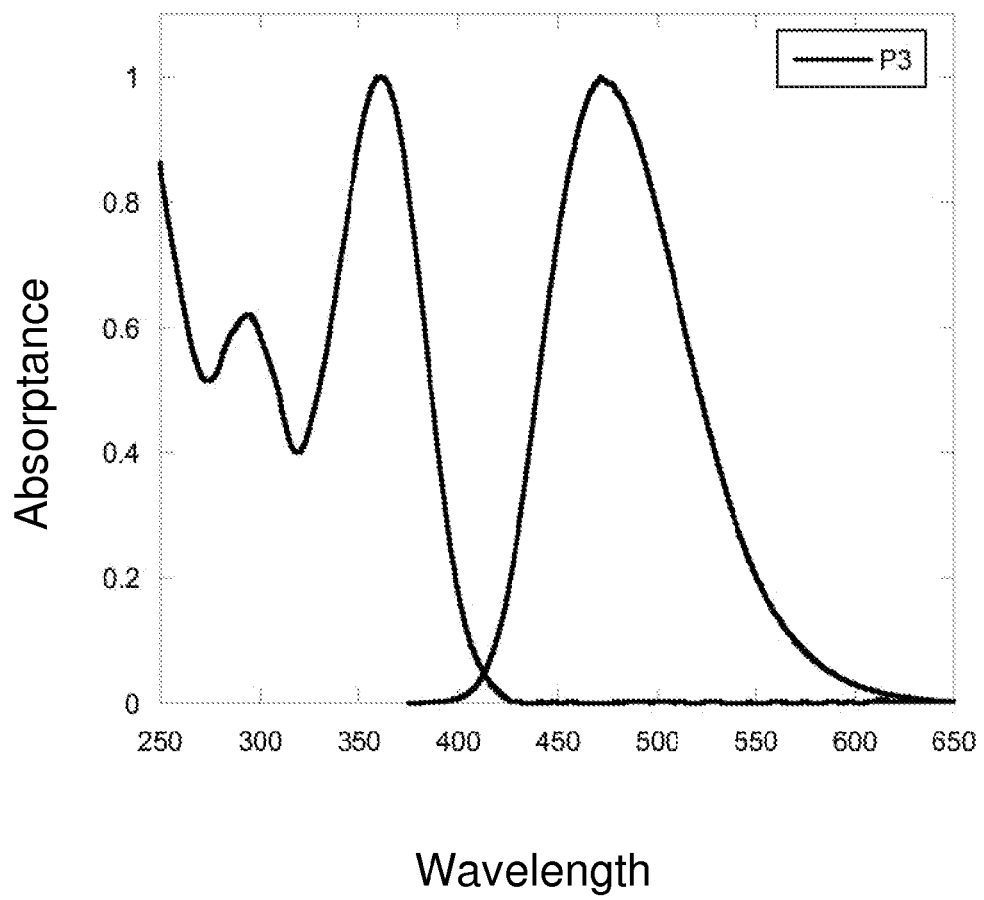
FIG. 1 is an absorption spectrum and an emission spectrum of the conjugated compound P3 having phenoxathiin of embodiment 5 in dichloromethane.
Figure 2:
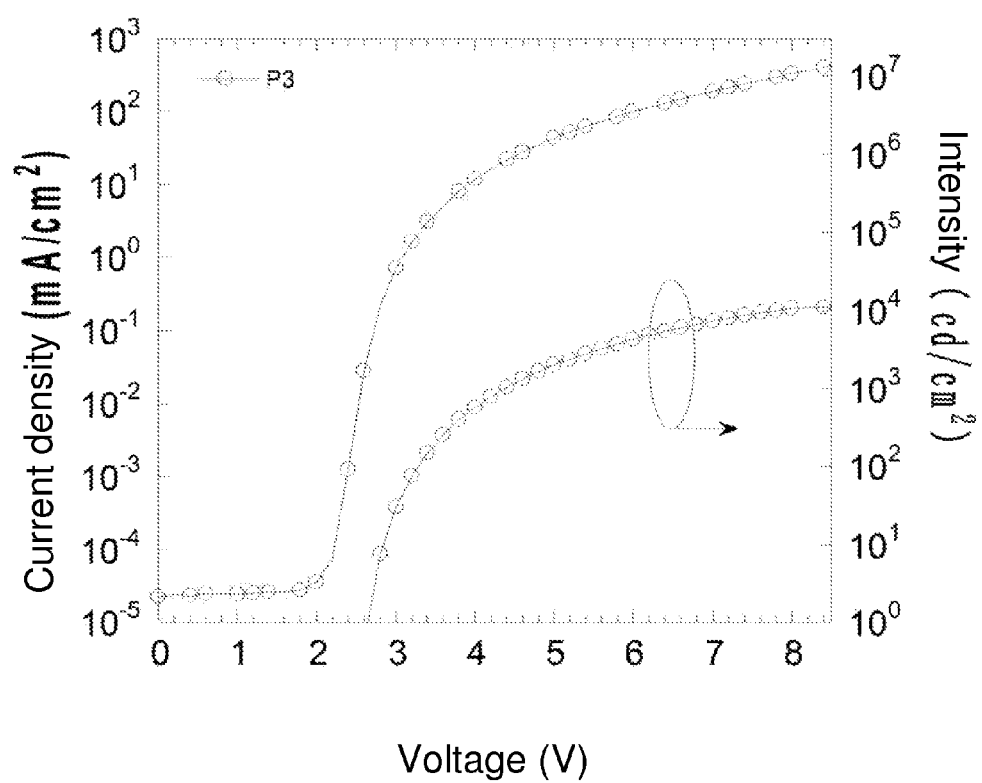
FIG. 2 is a diagram of current density-voltage-intensity of the OLED device when the conjugated compound P3 having phenoxathiin of embodiment 5 is used as the material of light emitting layer.
Figure 3:
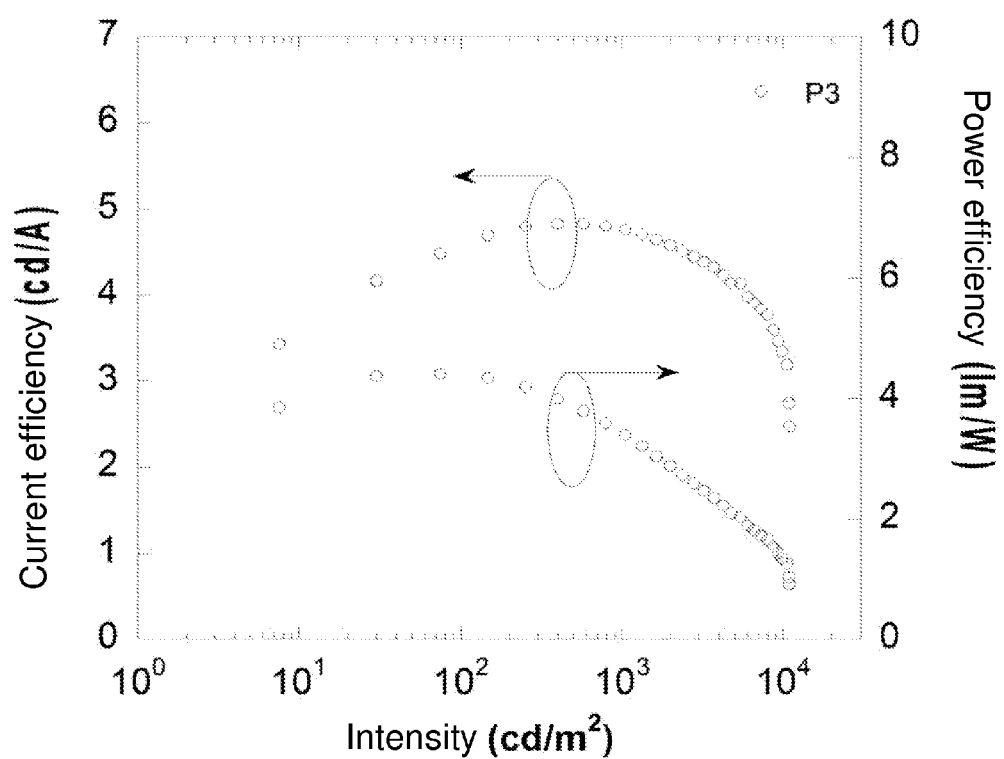
FIG. 3 a diagram of intensity-current efficiency-power efficiency of the OLED device when the conjugated compound P3 having phenoxathiin of embodiment 5 is used as the material of light emitting layer.

In the following description, the raw materials which are not indicated are commercial products. The method for preparing some of the compounds is described in the Embodiments. The following description with reference to the accompanying drawings is provided to clearly and completely explain the exemplary embodiments of the disclosure. It is apparent that the following embodiments are merely some embodiments of the disclosure rather than all embodiments of the disclosure.

Embodiment 1:

Preparation of intermediate M1 and M2 having phenoxathiin, the reactions are as below:

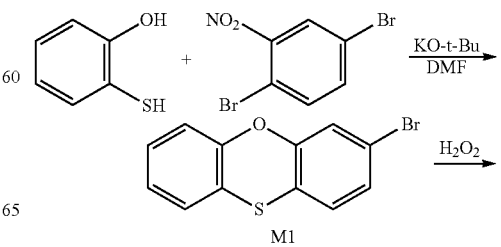

-continued

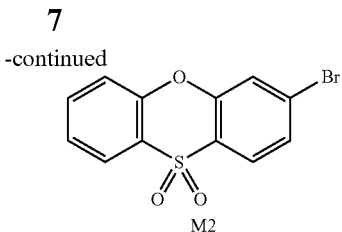

M1: 2-hydroxy-benzenethiol (3 g, 23.8 mmol) and 120 mL of anhydrous N,N-dimethyl formamide are incorporated into a 250 mL three-necked flask and are stirred under Ar. With the protection of air, potassium tert-butoxide (5.47 g, 48.7 mmol) is incorporated. After stirring for 0.5 hour, 2,5-dibromo nitrobenzne (7.01 g, 25 mmol) is slowly incorporated. After stirring for 20 minutes, the reactant is heated under reflux overnight. After most of the anhydrous N,N-dimethyl formamide being vaporized by a rotary concentrator, the product is extracted by deionized water and dichloromethane and is separated by silica gel chromatography for obtaining a white solid of M1 (4.2 g), and the yield is 63%.

M2: M1 and 50 mL of glacial acetic acid are incorporated into a 100 mL three-necked flask. After stirring, 10 mL of 30% hydrogen peroxide is incorporated. The reactant is heated under reflux overnight. After cooling, alcohol is incorporated. The reactant is vacuum filtrated. After drying, a white solid of M2 (4.57 g) is obtained. The yield is 97%.

Embodiment 2:

Preparation of intermediate M3 and M4 having phenoxathiin, the reactions are as below:

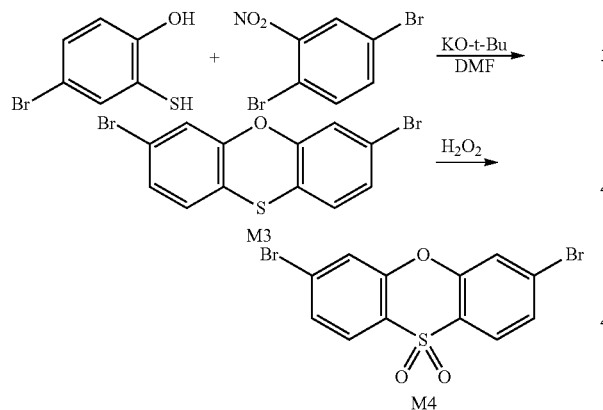

M3: 5-bromo-2-hydroxy-benzenethiol (5 g, 23.8 mmol) and 120 mL of anhydrous N,N-dimethyl formamide are incorporated into a 250 mL three-necked flask and are stirred under Ar. With the protection of air, potassium tert-butoxide (5.47 g, 48.7 mmol) is slowly incorporated. After stirring for 0.5 hour, 2,5-dibromo nitrobenzne (7.01 g, 25 mmol) is incorporated. After stirring for 20 minutes, the reactant is heated under reflux overnight. After most of the anhydrous N,N-dimethyl formamide being vaporized by a rotary concentrator, the product is extracted by deionized water and dichloromethane and is separated by silica gel chromatography for obtaining a white solid of M3 (4.6 g), and the yield is 66%.

M4: M3 and 50 mL of glacial acetic acid are incorporated into a 100 mL three-necked flask. After stirring, 10 mL of 30% hydrogen peroxide is incorporated. The reactant is heated under reflux overnight. After cooling, alcohol is incorporated. The reactant is vacuum filtrated. After drying, a white solid of M4 (4.50 g) is obtained. The yield is 97%.

Embodiment 3:

Preparation of a conjugated compound P1 having phenoxathiin, the reaction is as below:

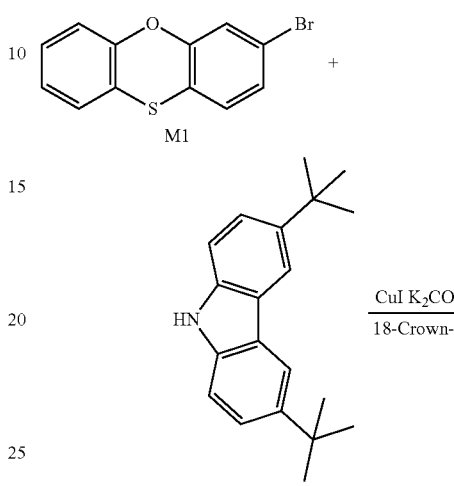

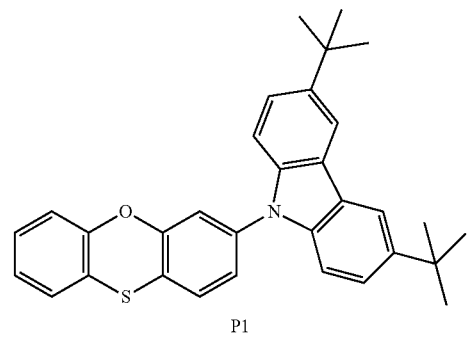

Under nitrogen, M1 (1.06 g, 3.5 mmol), 15 mL of N,N-dimethyl-N'-vinyl urea, CuI (0.56 g), potassium carbonate (1.40 g), 3,6-di-t-butyl-carbazole (1.17 g, 1.2 equ) and 18-crown-6 (0.21 g) are incorporated into a 100 mL three-necked flask. The reactant is stirred under 160° C. so as to undergo reactions for 24 hours. The solution is extracted by dichloromethane. The organic phase is collected, and then dried by anhydrous magnesium sulfate. Then, a vacuum filtration process is performed. The solvent of the filtered solution is removed by vacuum filtration. After separated by column chromatography, a white product is obtained. After drying, a high purity product is obtained by sublimation under vacuum condition (0.995 g, yield: 57%).

Embodiment 4:

Preparation of a conjugated compound P2 having phenoxathiin, the reaction is as below:

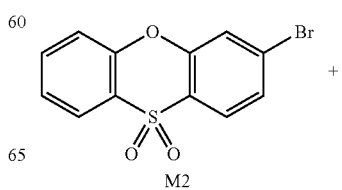

-continued

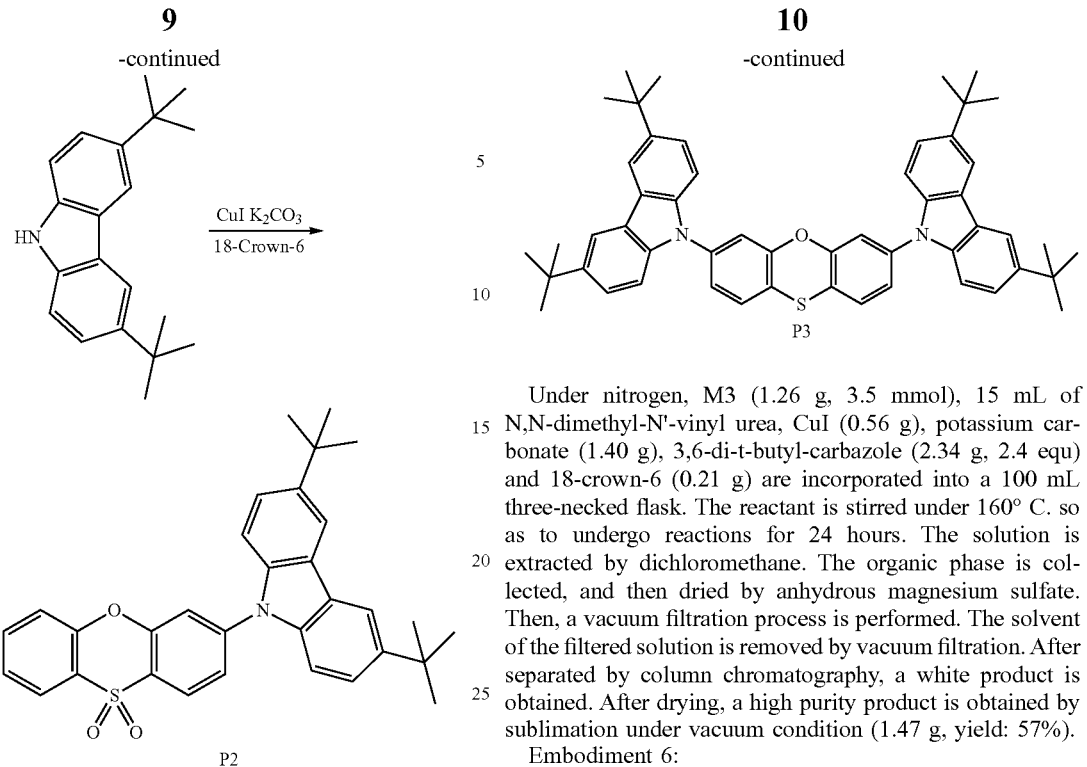

Under nitrogen, M2 (1.08 g, 3.5 mmol), 15 mL of N,N-dimethyl-N'-vinyl urea, CuI (0.56 g), potassium carbonate (1.40 g), 3,6-di-t-butyl-carbazole (1.17 g, 1.2 equ) and 18-crown-6 (0.21 g) are incorporated into a 100 mL three-necked flask. The reactant is stirred under 160° C. so as to undergo reactions for 24 hours. The solution is extracted by dichloromethane. The organic phase is collected, and then dried by anhydrous magnesium sulfate. Then, a vacuum filtration process is performed. The solvent of the filtered solution is removed by vacuum filtration. After separated by column chromatography, a white product is obtained. After drying, a high purity product is obtained by sublimation under vacuum condition (0.997 g, yield: 56%).

Embodiment 5:

Preparation of a conjugated compound P3 having phenoxathiin, the reaction is as below:

-continued

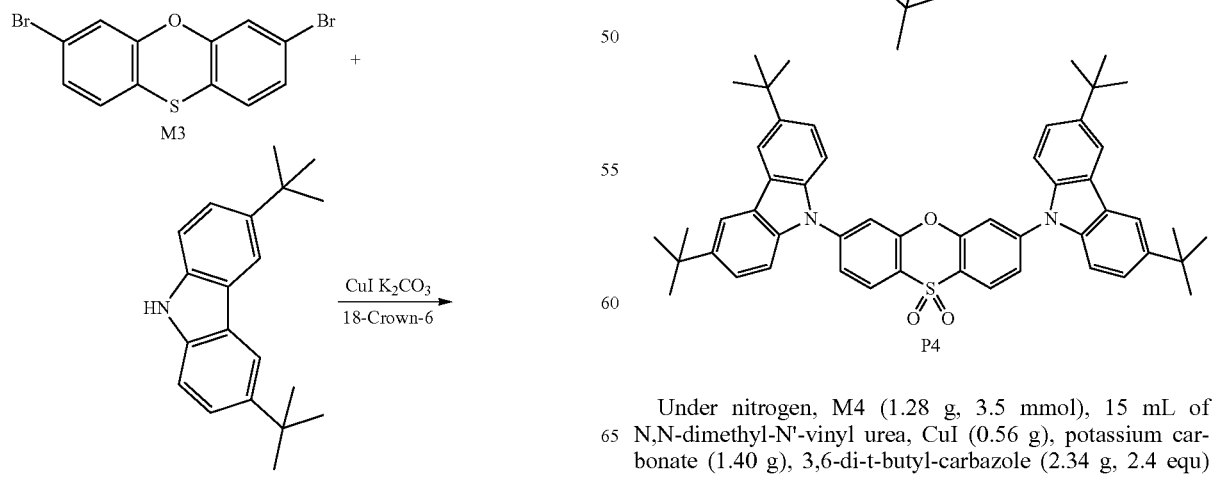

Under nitrogen, M3 (1.26 g, 3.5 mmol), 15 mL of N,N-dimethyl-N'-vinyl urea, CuI (0.56 g), potassium carbonate (1.40 g), 3,6-di-t-butyl-carbazole (2.34 g, 2.4 equ) and 18-crown-6 (0.21 g) are incorporated into a 100 mL three-necked flask. The reactant is stirred under 160° C. so as to undergo reactions for 24 hours. The solution is extracted by dichloromethane. The organic phase is collected, and then dried by anhydrous magnesium sulfate. Then, a vacuum filtration process is performed. The solvent of the filtered solution is removed by vacuum filtration. After separated by column chromatography, a white product is obtained. After drying, a high purity product is obtained by sublimation under vacuum condition (1.47 g, yield: 57%).

Embodiment 6:

Preparation of a conjugated compound P4 having phenoxathiin, the reaction is as below:

Under nitrogen, M4 (1.28 g, 3.5 mmol), 15 mL of N,N-dimethyl-N'-vinyl urea, CuI (0.56 g), potassium carbonate (1.40 g), 3,6-di-t-butyl-carbazole (2.34 g, 2.4 equ) and 18-crown-6 (0.21 g) are incorporated into a 100 mL three-necked flask. The reactant is stirred under 160° C. so as to undergo reactions for 24 hours. The solution is extracted by dichloromethane. The organic phase is collected, and then dried by anhydrous magnesium sulfate. Then, a vacuum filtration process is performed. The solvent of the filtered solution is removed by vacuum filtration. After separated by column chromatography, a white product is obtained. After drying, a high purity product is obtained by sublimation under vacuum condition (1.49 g, yield: 55%).

Embodiment 7:

Preparation of a conjugated compound P5 having phenoxathiin, the reaction is as below:

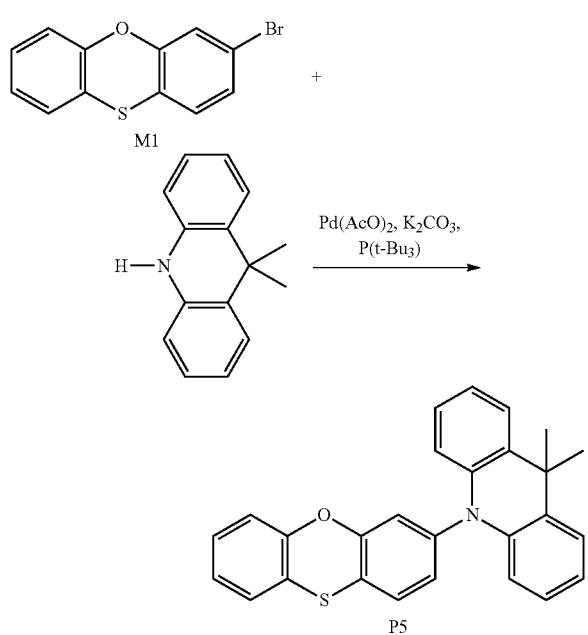

Under Ar, M1 (1.04 g, 3.5 mmol), 9,10-dihydro-9,9-dimethyl-acridine (3.5 mmol, 0.71 g), 100 mL of toluene, 60 mg of palladium acetate, tri-butyl phosphate (0.5 mmol, 0.11 g) and 0.75 g of potassium carbonate (0.75 g) are incorporated into a reaction flask. The reactant is stirred and heated under reflux overnight for 24 hours. After cooling, the mixture is poured into 200 mL water, and is extracted by dichloromethane. The organic phase is dried by anhydrous magnesium sulfate. After separation, the solvent is removed. A white solid is obtained after purification by silica gel chromatography. After drying, a high purity product is obtained by sublimation under vacuum condition (1.24 g, yield: 86%).

Embodiment 8:

Preparation of a conjugated compound P6 having phenoxathiin, the reaction is as below:

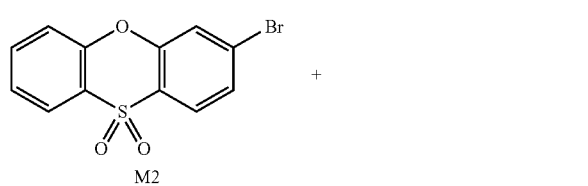

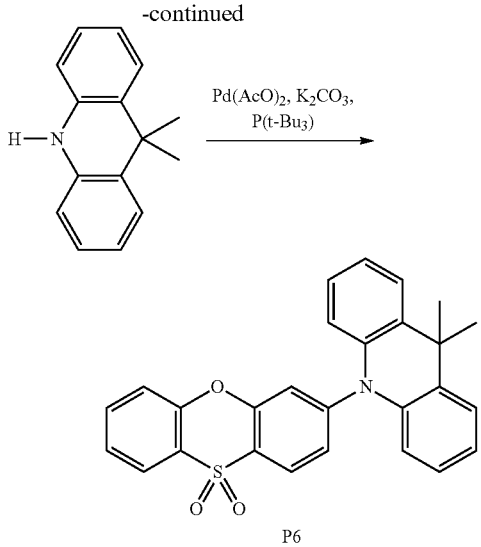

Under Ar, M2 (1.08 g, 3.5 mmol), 9,10-dihydro-9,9-dimethyl-acridine (3.5 mmol, 0.71 g), 100 mL of toluene, 60 mg of palladium acetate, tri-butyl phosphate (0.5 mmol, 0.11 g) and 0.75 g of potassium carbonate (0.75 g) are incorporated into a reaction flask. The reactant is stirred and heated under reflux overnight for 24 hours. After cooling, the mixture is poured into 200 mL water, and is extracted by dichloromethane. The organic phase is dried by anhydrous magnesium sulfate. After separation, the solvent is removed. A white solid is obtained after purification by silica gel chromatography. After drying, a high purity product is obtained by sublimation under vacuum condition (1.29 g, yield: 84%).

Embodiment 9:

Preparation of a conjugated compound P7 having phenoxathiin, the reaction is as below:

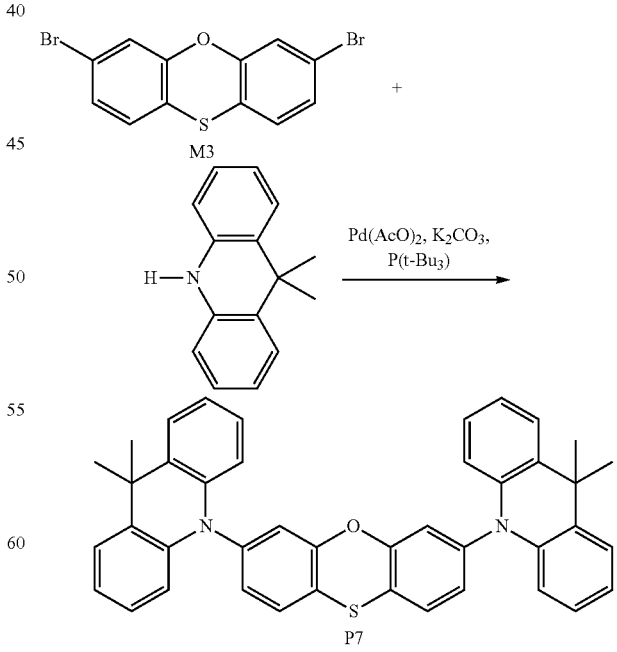

Under nitrogen, M3 (1.25 g, 3.5 mmol), 9,10-dihydro-9, 9-dimethyl-acridine (7 mmol, 1.4 g), 100 mL of toluene, 60 mg of palladium acetate, tri-butyl phosphate (0.5 mmol, 0.11 g) and 0.75 g of potassium carbonate (0.75 g) are incorporated into a flask. The reactant is stirred and heated under reflux overnight for 24 hours. Then, the mixture is extracted by dichloromethane. The organic phase is collected, and then dried by anhydrous magnesium sulfate. Then, a vacuum filtration process is performed. The solvent of the filtered solution is removed by vacuum filtration. After separated by column chromatography, a white product is obtained. After drying, a high purity product is obtained by sublimation under vacuum condition (2.01 g, yield: 85%).

Embodiment 10:

Preparation of a conjugated compound P8 having phenoxathiin, the reaction is as below:

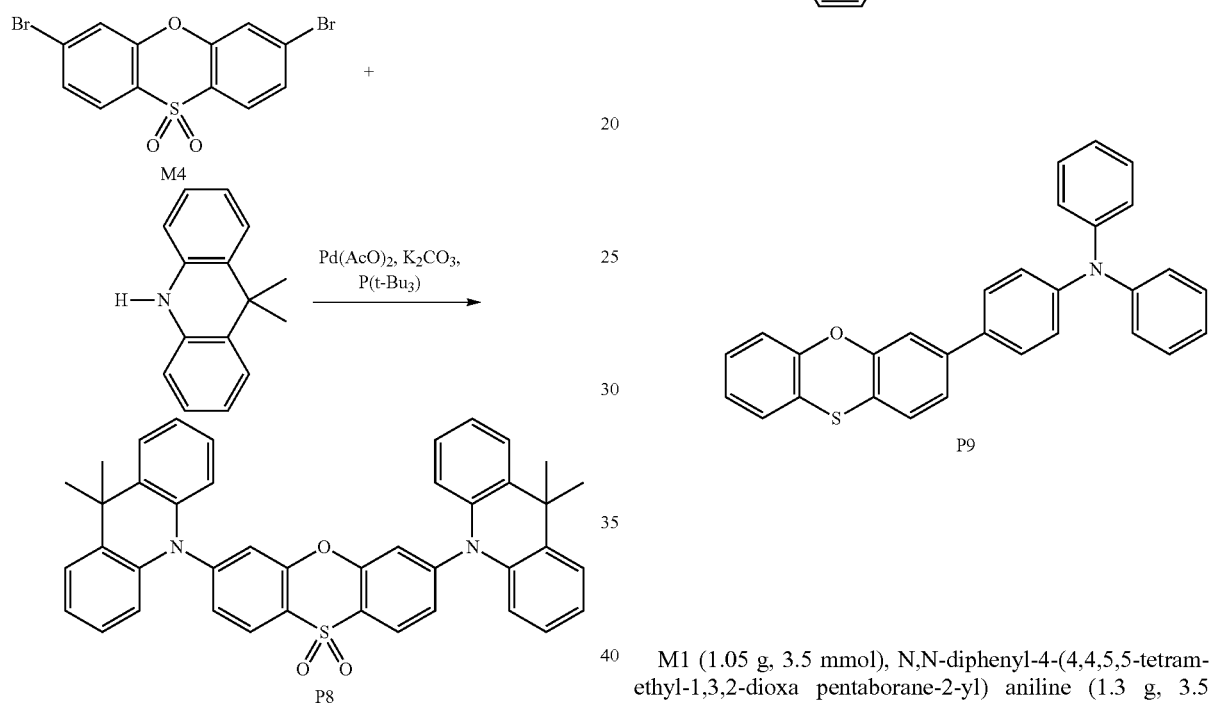

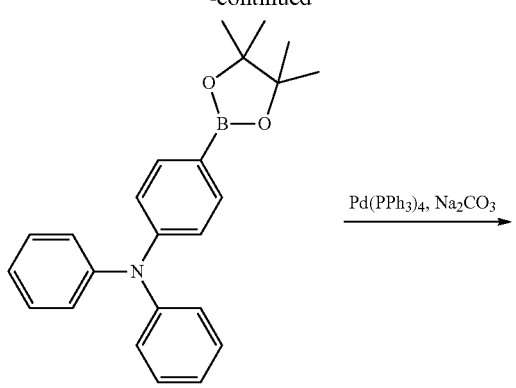

Under nitrogen, M4 (1.28 g, 3.5 mmol), 9,10-dihydro-9,9-dimethyl-acridine (7 mmol, 1.4 g), 100 mL of toluene, 60 mg of palladium acetate, tri-butyl phosphate (0.5 mmol, 0.11 g) and 0.75 g of potassium carbonate (0.75 g) are incorporated into a flask. The reactant is stirred and heated under reflux overnight for 24 hours. Then, the mixture is extracted by dichloromethane. The organic phase is collected, and then dried by anhydrous magnesium sulfate. Then, a vacuum filtration process is performed. The solvent of the filtered solution is removed by vacuum filtration. After separated by column chromatography, a white product is obtained. After drying, a high purity product is obtained by sublimation under vacuum condition (2.0 g, yield: 87%).

Embodiment 11:

Preparation of a conjugated compound P9 having phenoxathiin, the reaction is as below:

M1 (1.05 g, 3.5 mmol), N,N-diphenyl-4-(4,4,5,5-tetramethyl-1,3,2-dioxa pentaborane-2-yl) aniline (1.3 g, 3.5 mmol), 120 mL of toluene, 40 mL of ethanol and 30 mL of 2M potassium carbonate are incorporated into a 250 mL single-neck flask. 100 mg of triphenylphosphine Pd(0) is incorporated. A ventilation process is performed for 30 minutes for replacing the oxygen in the system. After the ventilation process, the system is sealed and is heated for undergoing reaction under 90-100° C. for 18-24 hours. After cooling, the mixture is extracted by dichloromethane. The organic phase is dried by anhydrous magnesium sulfate. After separated by column chromatography, wherein the ratio of petroleum ether to dichloromethane is 1:1, a white solid is obtained (1.48 g, yield: 91%).

Embodiment 12:

Preparation of a conjugated compound P10 having phenoxathiin, the reaction is as below:

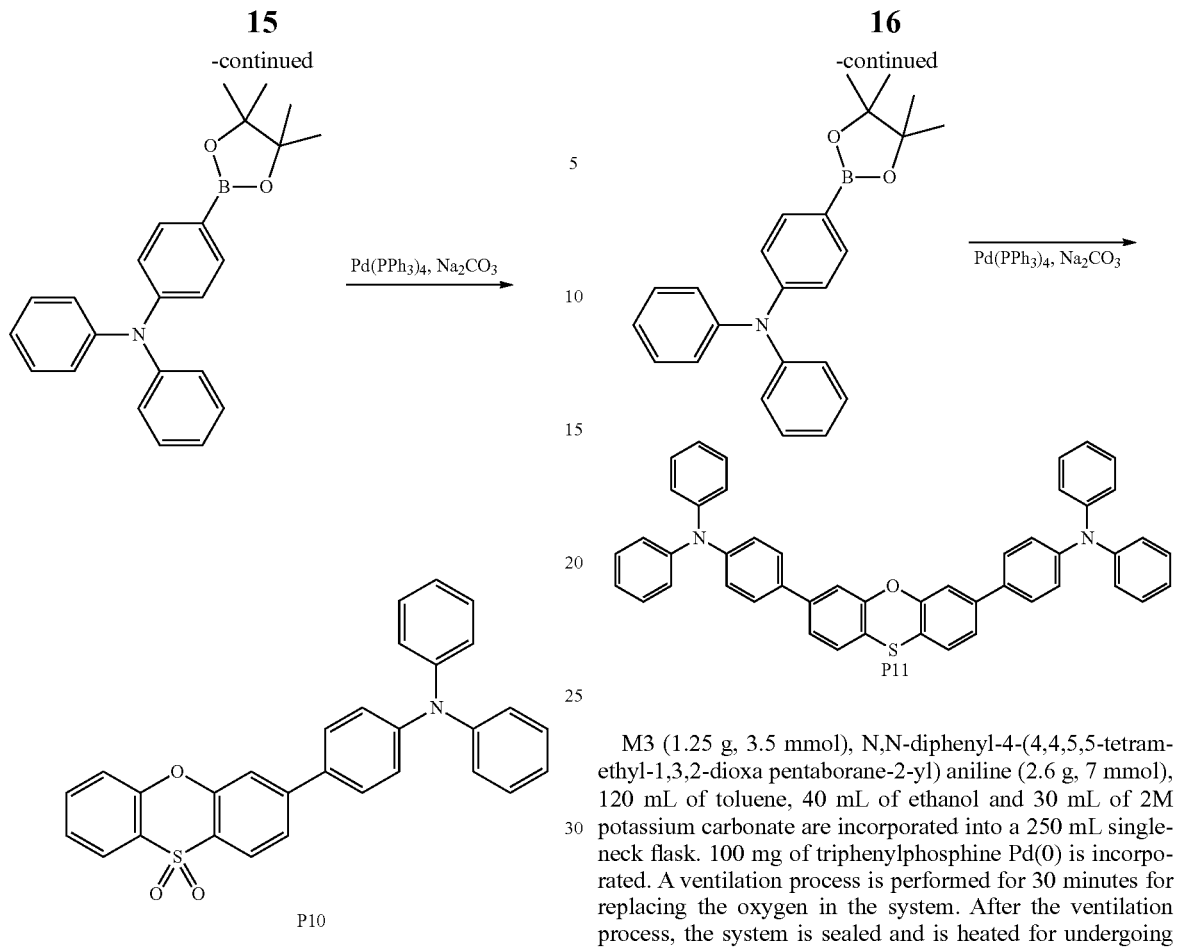

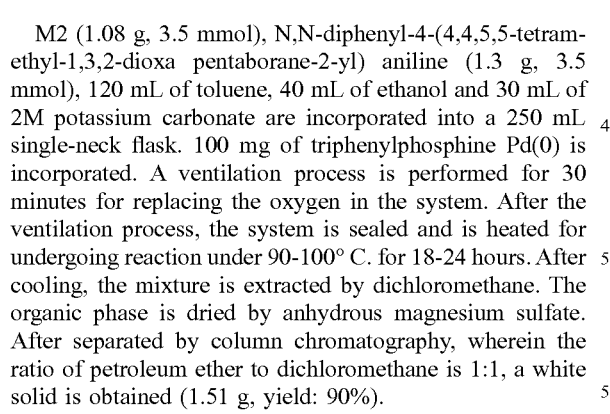

P10

M2 (1.08 g, 3.5 mmol), N,N-diphenyl-4-(4,4,5,5-tetramethyl-1,3,2-dioxa pentaborane-2-yl) aniline (1.3 g, 3.5 mmol), 120 mL of toluene, 40 mL of ethanol and 30 mL of 2M potassium carbonate are incorporated into a 250 mL single-neck flask. 100 mg of triphenylphosphine Pd(0) is incorporated. A ventilation process is performed for 30 minutes for replacing the oxygen in the system. After the ventilation process, the system is sealed and is heated for undergoing reaction under 90-100° C. for 18-24 hours. After cooling, the mixture is extracted by dichloromethane. The organic phase is dried by anhydrous magnesium sulfate. After separated by column chromatography, wherein the ratio of petroleum ether to dichloromethane is 1:1, a white solid is obtained (1.51 g, yield: 90%).

Embodiment 13:

Preparation of a conjugated compound P11 having phenoxathiin, the reaction is as below:

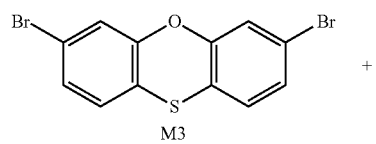

M3 (1.25 g, 3.5 mmol), N,N-diphenyl-4-(4,4,5,5-tetramethyl-1,3,2-dioxa pentaborane-2-yl) aniline (2.6 g, 7 mmol), 120 mL of toluene, 40 mL of ethanol and 30 mL of 2M potassium carbonate are incorporated into a 250 mL single-neck flask. 100 mg of triphenylphosphine Pd(0) is incorporated. A ventilation process is performed for 30 minutes for replacing the oxygen in the system. After the ventilation process, the system is sealed and is heated for undergoing reaction under 90-100° C. for 18-24 hours. After cooling, the mixture is extracted by dichloromethane. The organic phase is dried by anhydrous magnesium sulfate. After separated by column chromatography, wherein the ratio of petroleum ether to dichloromethane is 1:1, a white solid is obtained (2.10 g, yield: 91%).

Embodiment 14:

Preparation of a conjugated compound P12 having phenoxathiin, the reaction is as below:

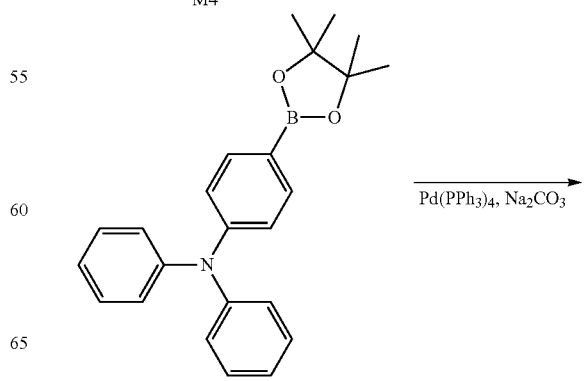

-continued

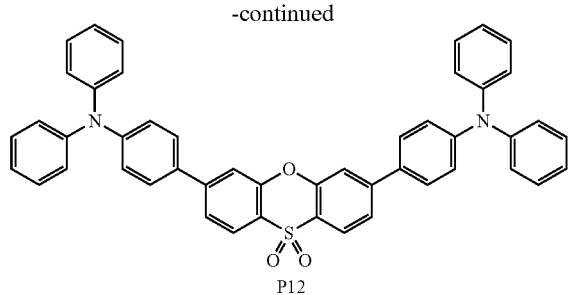

P12

M4 (1.28 g, 3.5 mmol), N,N-diphenyl-4-(4,4,5,5-tetramethyl-1,3,2-dioxa pentaborane-2-yl) aniline (2.6 g, 7 mmol), 120 mL of toluene, 40 mL of ethanol and 30 mL of 2M potassium carbonate are incorporated into a 250 mL single-neck flask. 100 mg of triphenylphosphine Pd(0) is incorporated. A ventilation process is performed for 30 minutes for replacing the oxygen in the system. After the ventilation process, the system is sealed and is heated for undergoing reaction under 90-100° C. for 18-24 hours. After cooling, the mixture is extracted by dichloromethane. The organic phase is dried by anhydrous magnesium sulfate. After separated by column chromatography, wherein the ratio of petroleum ether to dichloromethane is 1:1, a white solid is obtained (2.15 g, yield: 92%).

Embodiment 15:

Preparation of a conjugated compound P13 having phenoxathiin, the reaction is as below:

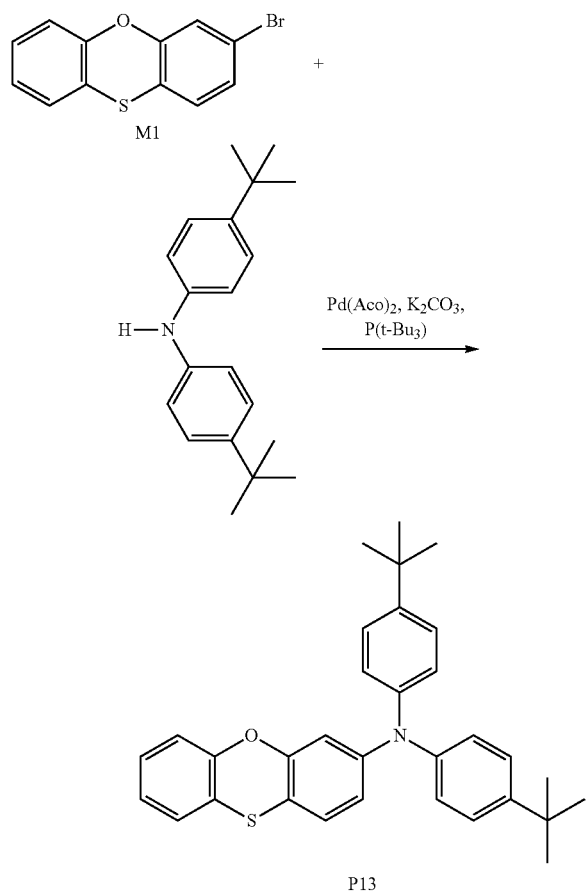

Under Ar, M1 (1.05 g, 3.5 mmol), bis-(4-tert-butylphenyl) amine (3.5 mmol, 1.0 g), 100 mL of toluene, 60 mg of palladium acetate, tri-butyl phosphate (0.5 mmol, 0.11 g) and 0.75 g of potassium carbonate (0.75 g) are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.50 g, yield: 85%).

Embodiment 16:

Preparation of a conjugated compound P14 having phenoxathiin, the reaction is as below:

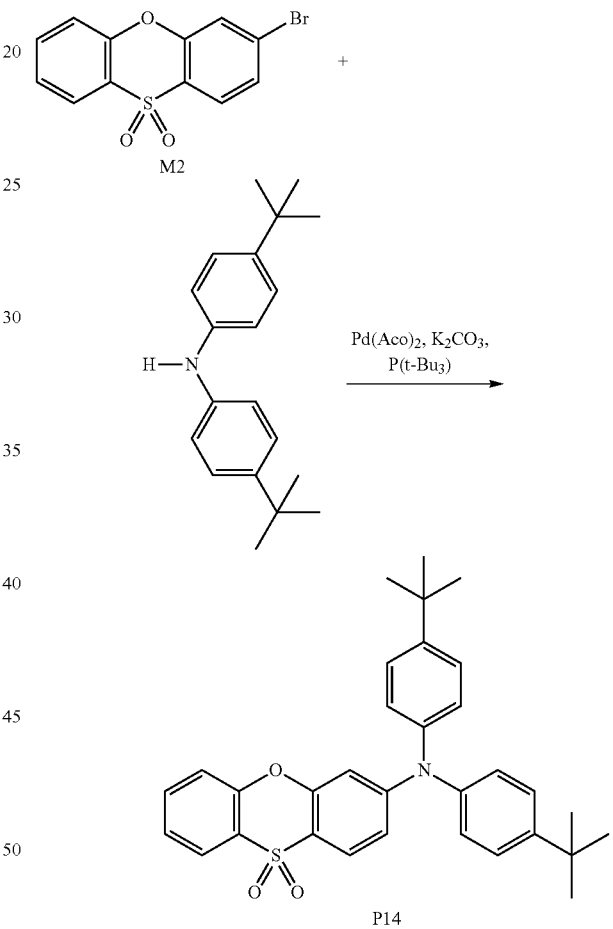

Under Ar, M2 (1.08 g, 3.5 mmol), bis-(4-tert-butylphenyl) amine (3.5 mmol, 1.0 g), 100 mL of toluene, 60 mg of palladium acetate, tri-butyl phosphate (0.5 mmol, 0.11 g) and 0.75 g of potassium carbonate (0.75 g) are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.50 g, yield: 85%).

Embodiment 17:

Preparation of a conjugated compound P15 having phenoxathiin, the reaction is as below:

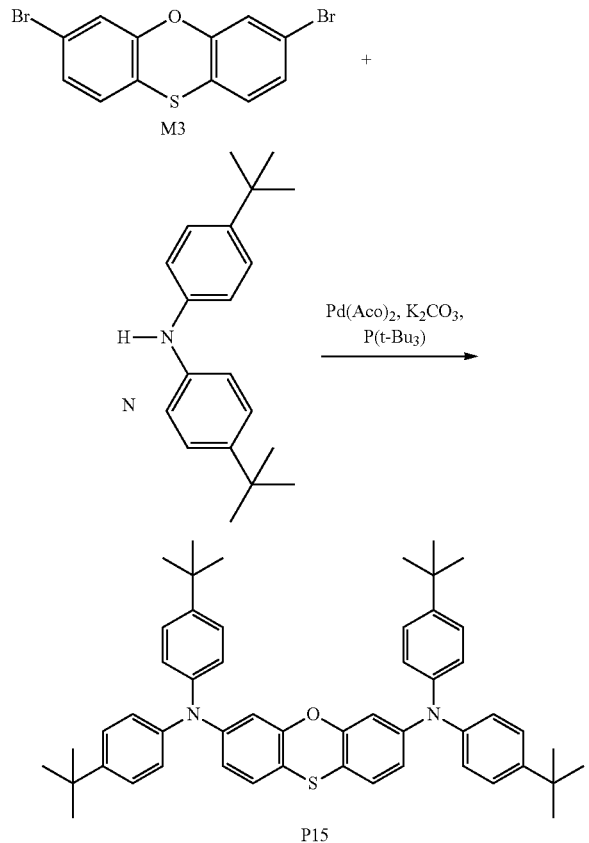

Under Ar, M3 (1.20 g, 3.5 mmol), bis-(4-tert-butylphenyl) amine (7 mmol, 2.0 g), 100 mL of toluene, 60 mg of palladium acetate, tri-butyl phosphate (0.5 mmol, 0.11 g) and 0.75 g of potassium carbonate (0.75 g) are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (2.9 g, yield: 85%).

Embodiment 18:

Preparation of a conjugated compound P16 having phenoxathiin, the reaction is as below:

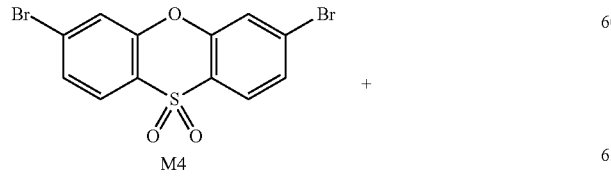

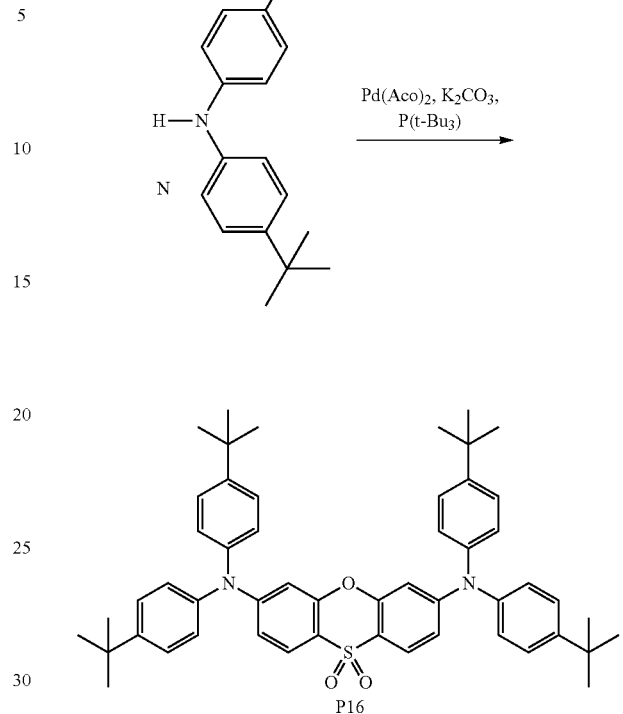

Under Ar, M4 (1.28 g, 3.5 mmol), bis-(4-tert-butylphenyl) amine (7 mmol, 2.0 g), 100 mL of toluene, 60 mg of palladium acetate, tri-butyl phosphate (0.5 mmol, 0.11 g) and 0.75 g of potassium carbonate (0.75 g) are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (2.94 g, yield: 83%).

Embodiment 19:

Preparation of a conjugated compound P17 having phenoxathiin, the reaction is as below:

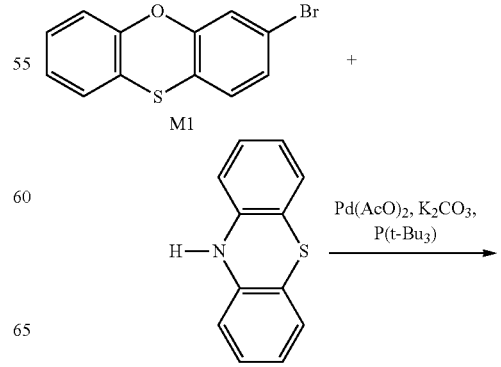

-continued

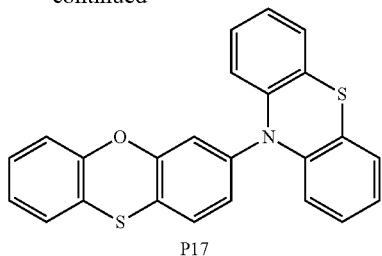

P17

Under Ar, M1 (1.05 g, 3.5 mmol), phenothiazine (3.5 mmol, 0.70 g), 100 mL of toluene, 60 mg of palladium acetate, tri-butyl phosphate (0.5 mmol, 0.11 g) and 0.75 g of potassium carbonate (0.75 g) are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.21 g, yield: 84%).

Embodiment 20:

Preparation of a conjugated compound P18 having phenoxathiin, the reaction is as below:

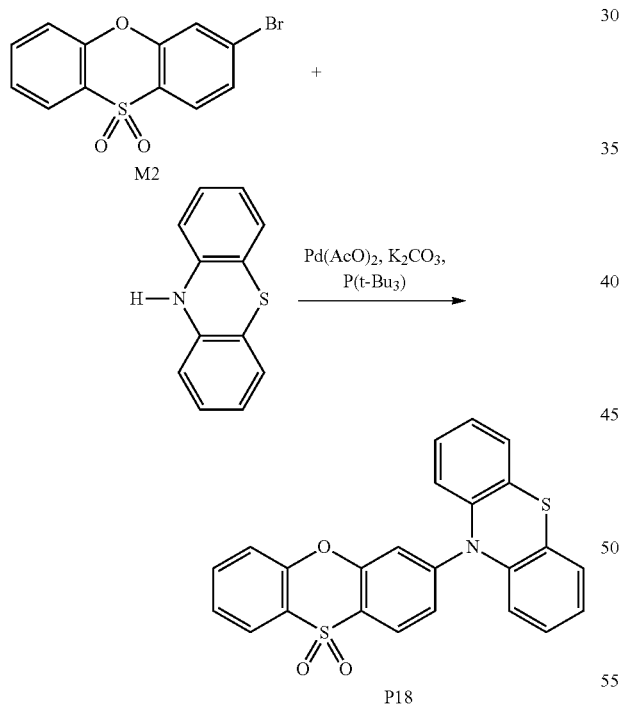

P18

Under Ar, M2 (1.08 g, 3.5 mmol), phenothiazine (3.5 mmol, 0.70 g), 100 mL of toluene, 60 mg of palladium acetate, tri-butyl phosphate (0.5 mmol, 0.11 g) and 0.75 g of potassium carbonate (0.75 g) are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.21 g, yield: 84%).

Embodiment 21:

Preparation of a conjugated compound P19 having phenoxathiin, the reaction is as below:

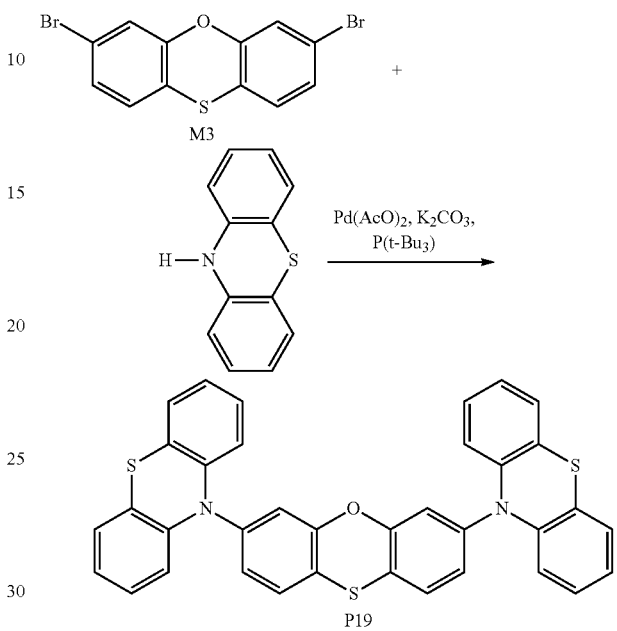

P19

Under Ar, M3 (1.20 g, 3.5 mmol), phenothiazine (7 mmol, 1.40 g), 100 mL of toluene, 60 mg of palladium acetate, tri-butyl phosphate (0.5 mmol, 0.11 g) and 0.75 g of potassium carbonate (0.75 g) are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.89 g, yield: 84%).

Embodiment 22:

Preparation of a conjugated compound P20 having phenoxathiin, the reaction is as below:

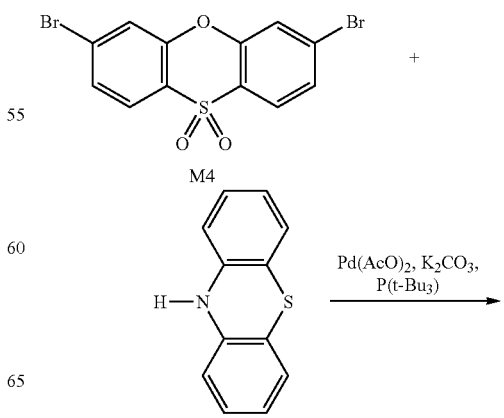

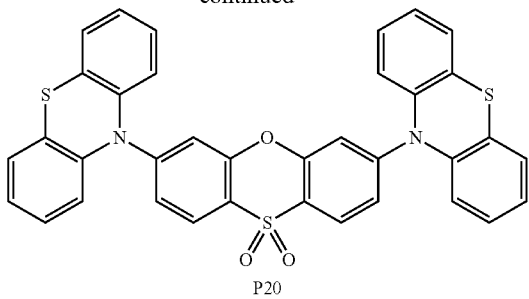

P20

Under Ar, M4 (1.08 g, 3.5 mmol), phenothiazine (7 mmol, 1.40 g), 100 mL of toluene, 60 mg of palladium acetate, tri-butyl phosphate (0.5 mmol, 0.11 g) and 0.75 g of potassium carbonate (0.75 g) are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.94 g, yield: 85%).

Embodiment 23:

Preparation of a conjugated compound P21 having phenoxathiin, the reaction is as below:

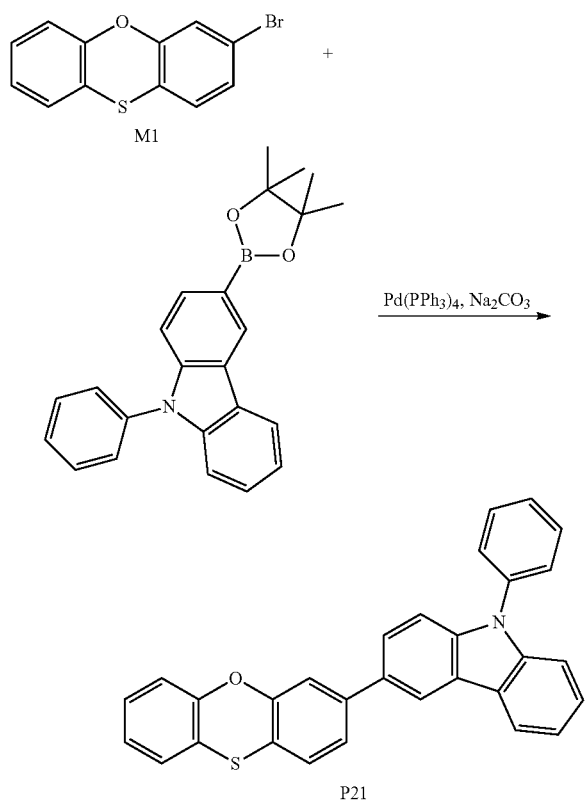

P21

Under Ar, M1 (1.05 g, 3.5 mmol), 9-phenyl-3-(4,4,5,5-tetramethyl-1,3,2-dioxa pentaborane 2-yl) carbazole (3.5 mmol, 1.3 g), 30 mL of toluene, 15 mL of tetrahydrofurane, 20 mL of 10 wt % sodium carbonate and 50 mg of tetrakis (triphenylphosphine) palladium are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.42 g, yield: 86%).

Embodiment 24:

Preparation of a conjugated compound P22 having phenoxathiin, the reaction is as below:

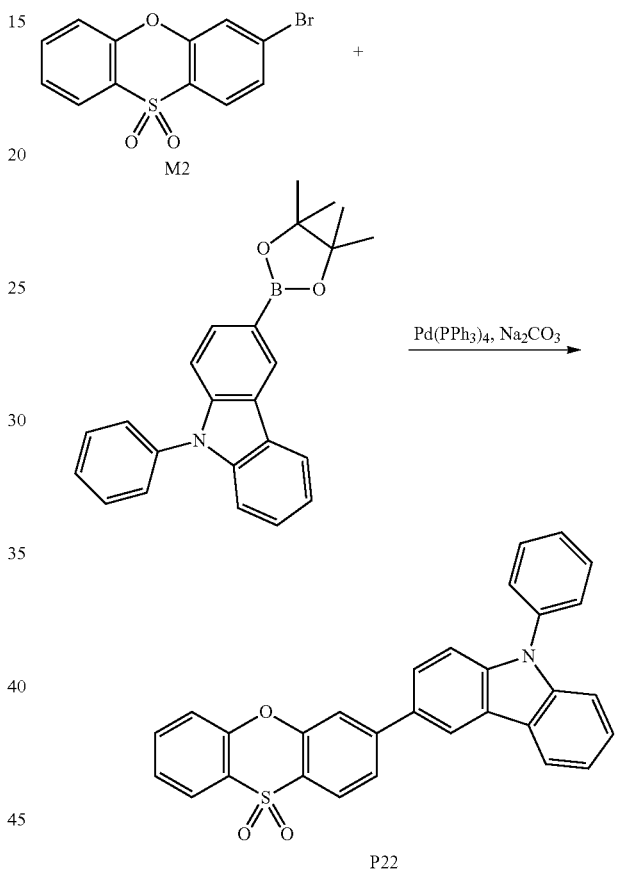

P22

Under Ar, M2 (1.08 g, 3.5 mmol), 9-phenyl-3-(4,4,5,5-tetramethyl-1,3,2-dioxa pentaborane 2-yl) carbazole (3.5 mmol, 1.3 g), 30 mL of toluene, 15 mL of tetrahydrofurane, 20 mL of 10 wt % sodium carbonate and 50 mg of tetrakis (triphenylphosphine) palladium are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.40 g, yield: 85%).

Embodiment 25:

Preparation of a conjugated compound P23 having phenoxathiin, the reaction is as below:

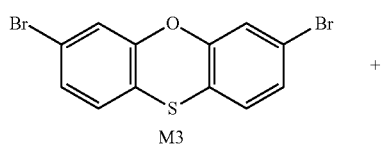

M3

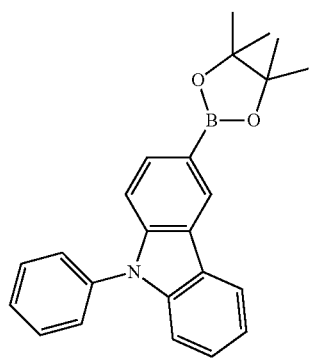

Pd(PPh₃)₄, Na₂CO₃

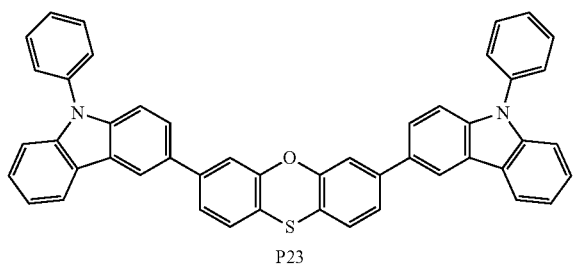

P23

Under Ar, M3 (1.25 g, 3.5 mmol), 9-phenyl-3-(4,4,5,5-tetramethyl-1,3,2-dioxa pentaborane 2-yl) carbazole (7 mmol, 2.6 g), 30 mL of toluene, 15 mL of tetrahydrofurane, 20 mL of 10 wt % sodium carbonate and 50 mg of tetrakis (triphenylphosphine) palladium are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (2.00 g, yield: 85%).

Embodiment 26:

Preparation of a conjugated compound P24 having phenoxathiin, the reaction is as below:

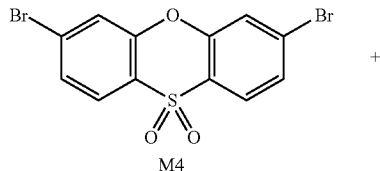

M4

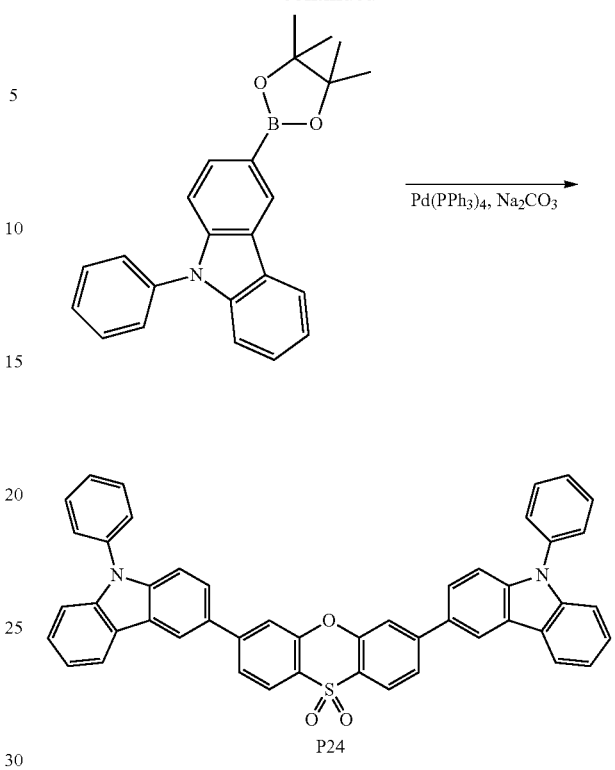

Pd(PPh₃)₄, Na₂CO₃

P24

Under Ar, M4 (1.28 g, 3.5 mmol), 9-phenyl-3-(4,4,5,5-tetramethyl-1,3,2-dioxa pentaborane 2-yl) carbazole (7 mmol, 2.6 g), 30 mL of toluene, 15 mL of tetrahydrofurane, 20 mL of 10 wt % sodium carbonate and 50 mg of tetrakis (triphenylphosphine) palladium are incorporated into a reaction flask. The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (2.06 g, yield: 86%).

Embodiment 27:

Preparation of a conjugated compound P25 having phenoxathiin, the reaction is as below:

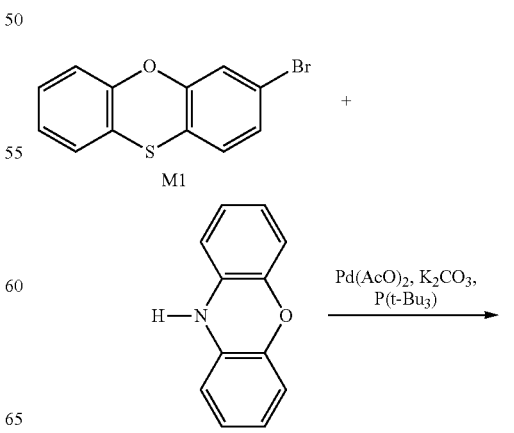

Pd(AcO)₂, K₂CO₃, P(t-Bu₃)

-continued

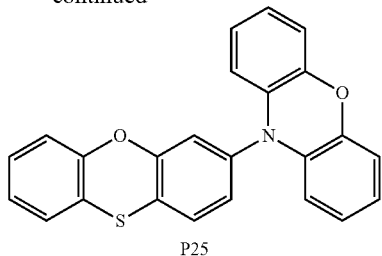

P25

Under Ar, M1 (1.05 g, 3.5 mmol), phenoxazine (3.5 mmol, 0.68 g), 100 mL of toluene, 60 mg of palladium acetate, tri-butyl phosphate (0.5 mmol, 0.11 g) and 0.75 g of potassium carbonate (0.75 g) are incorporated into a reaction flask The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.21 g, yield: 84%).

Embodiment 28:

Preparation of a conjugated compound P26 having phenoxathiin, the reaction is as below:

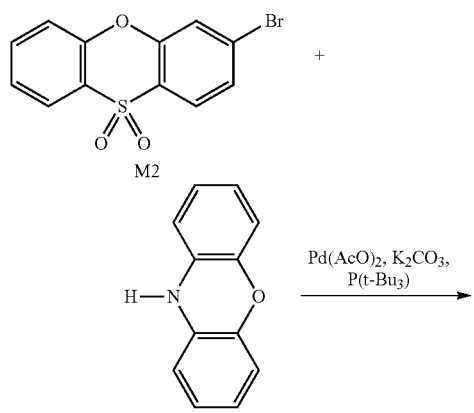

P26

Under Ar, M2 (1.05 g, 3.5 mmol), phenoxazine (3.5 mmol, 0.68 g), 100 mL of toluene, 60 mg of palladium acetate, tri-butyl phosphate (0.5 mmol, 0.11 g) and 0.75 g of potassium carbonate (0.75 g) are incorporated into a reaction flask The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.21 g, yield: 84%).

Embodiment 29:

Preparation of a conjugated compound P27 having phenoxathiin, the reaction is as below:

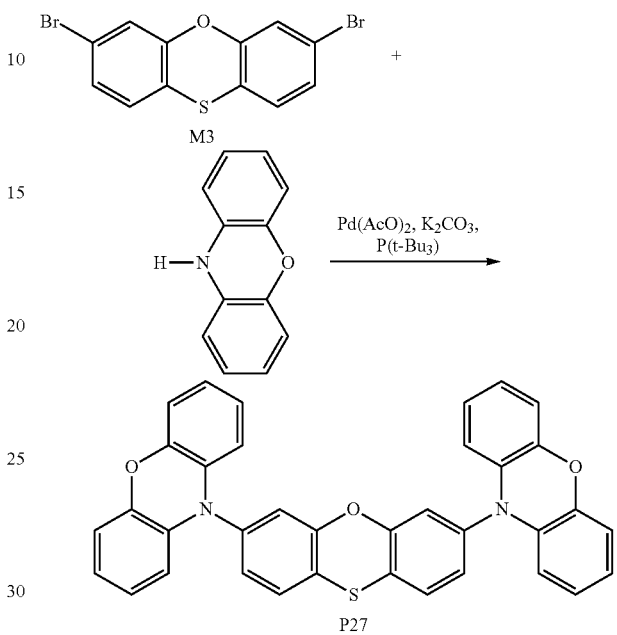

P27

Under Ar, M3 (1.25 g, 3.5 mmol), phenoxazine (7 mmol, 1.36 g), 100 mL of toluene, 60 mg of palladium acetate, tri-butyl phosphate (0.5 mmol, 0.11 g) and 0.75 g of potassium carbonate (0.75 g) are incorporated into a reaction flask The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.65 g, yield: 84%).

Embodiment 30:

Preparation of a conjugated compound P28 having phenoxathiin, the reaction is as below:

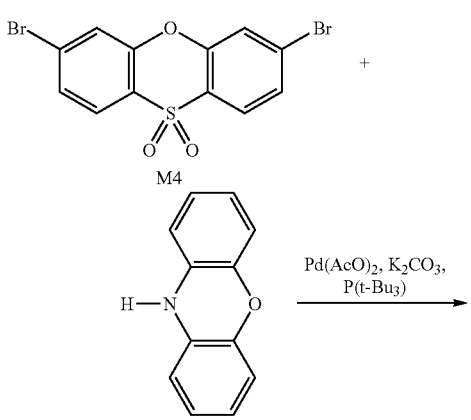

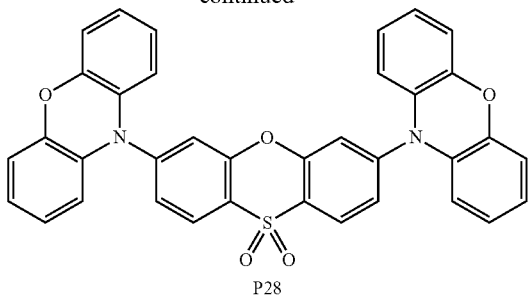

P28

Under Ar, M4 (1.28 g, 3.5 mmol), phenoxazine (7 mmol, 1.36 g), 100 mL of toluene, 60 mg of palladium acetate, tri-butyl phosphate (0.5 mmol, 0.11 g) and 0.75 g of potassium carbonate (0.75 g) are incorporated into a reaction flask The reactant is stirred and heated under reflux overnight for 24 hours. After cooling, the mixture is poured into 200 mL of water and is extracted by dichloromethane. The organic phase is dried by anhydrous magnesium sulfate. The solvent of the filtered solution is removed. After separated by silica gel chromatography, a white product is obtained. After drying, a high purity product is obtained by sublimation under vacuum condition (1.68 g, yield: 83%).

Embodiment 31:

Preparation of a conjugated compound P29 having phenoxathiin, the reaction is as below:

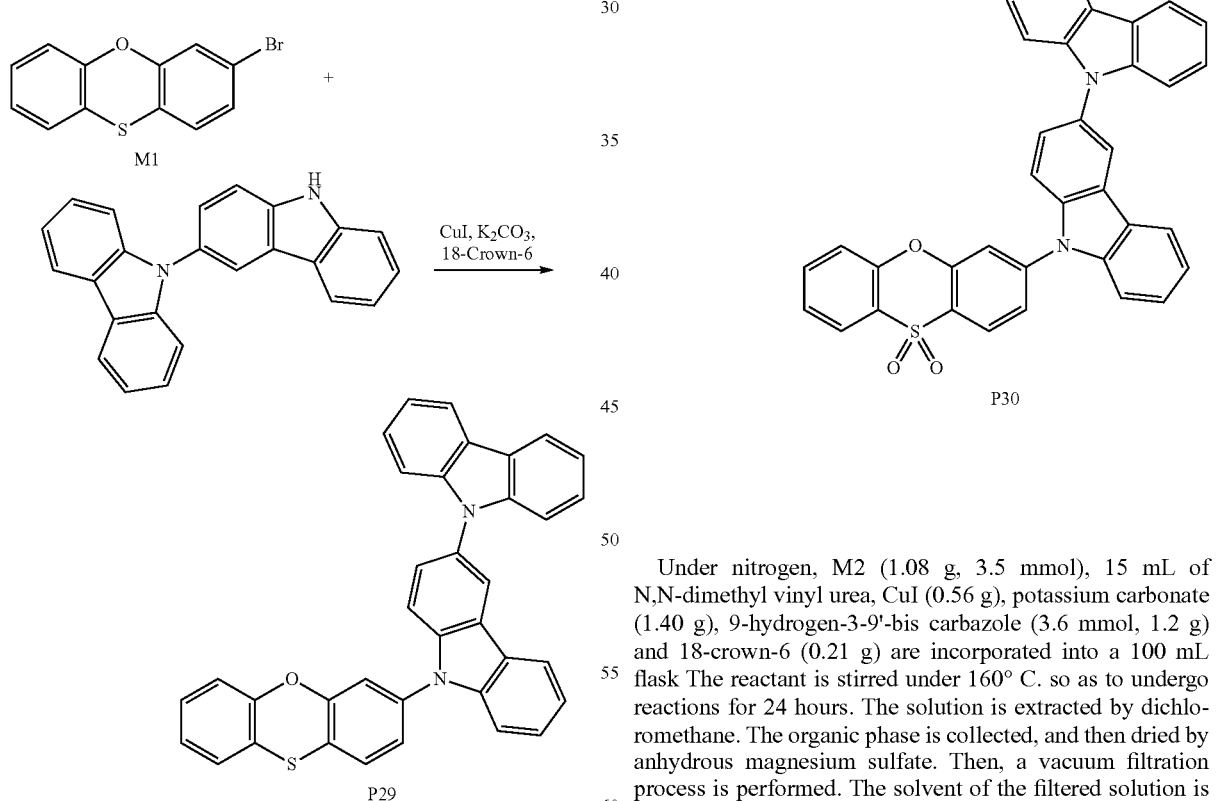

P29

Under nitrogen, M1 (1.05 g, 3.5 mmol), 15 mL of N,N-dimethyl vinyl urea, CuI (0.56 g), potassium carbonate (1.40 g), 9-hydrogen-3-9'-bis carbazole (3.6 mmol, 1.2 g) and 18-crown-6 (0.21 g) are incorporated into a 100 mL flask The reactant is stirred under 160° C. so as to undergo reactions for 24 hours. The solution is extracted by dichloromethane. The organic phase is collected, and then dried by anhydrous magnesium sulfate. Then, a vacuum filtration process is performed. The solvent of the filtered solution is removed by vacuum filtration. After separated by column chromatography, a white product is obtained. After drying, a high purity product is obtained by sublimation under vacuum condition (0.997 g, yield: 56%).

Embodiment 32:

Preparation of a conjugated compound P30 having phenoxathiin, the reaction is as below:

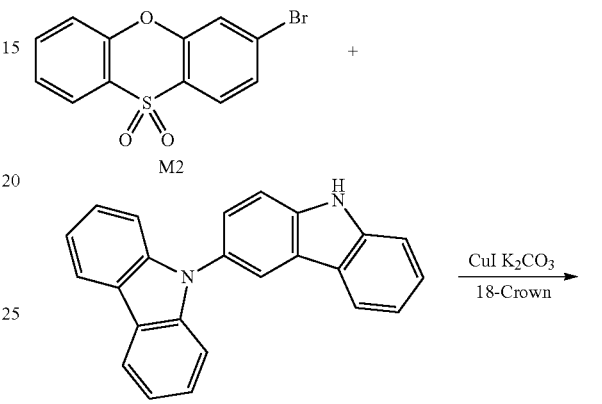

P30

Under nitrogen, M2 (1.08 g, 3.5 mmol), 15 mL of N,N-dimethyl vinyl urea, CuI (0.56 g), potassium carbonate (1.40 g), 9-hydrogen-3-9'-bis carbazole (3.6 mmol, 1.2 g) and 18-crown-6 (0.21 g) are incorporated into a 100 mL flask The reactant is stirred under 160° C. so as to undergo reactions for 24 hours. The solution is extracted by dichloromethane. The organic phase is collected, and then dried by anhydrous magnesium sulfate. Then, a vacuum filtration process is performed. The solvent of the filtered solution is removed by vacuum filtration. After separated by column chromatography, a white product is obtained. After drying, a high purity product is obtained by sublimation under vacuum condition (1.00 g, yield: 57%).

Embodiment 33:

Preparation of a conjugated compound P31 having phenoxathiin, the reaction is as below:

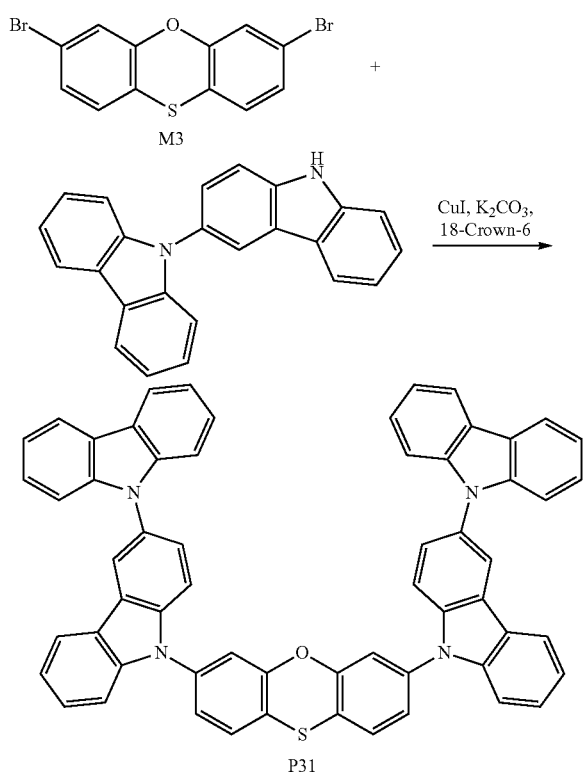

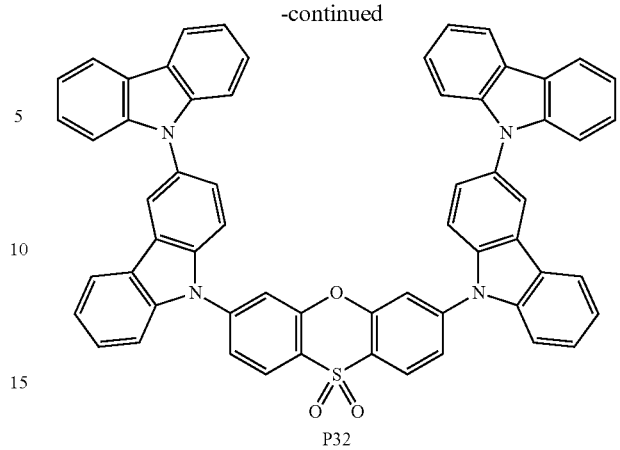

Under nitrogen, M3 (1.25 g, 3.5 mmol), 15 mL of N,N-dimethyl vinyl urea, CuI (0.56 g), potassium carbonate (1.40 g), 9-hydrogen-3-9'-bis carbazole (7.2 mmol, 2.4 g) and 18-crown-6 (0.21 g) are incorporated into a 100 mL flask The reactant is stirred under 160° C. so as to undergo reactions for 24 hours. The solution is extracted by dichloromethane. The organic phase is collected, and then dried by anhydrous magnesium sulfate. Then, a vacuum filtration process is performed. The solvent of the filtered solution is removed by vacuum filtration. After separated by column chromatography, a white product is obtained. After drying, a high purity product is obtained by sublimation under vacuum condition (1.63 g, yield: 56%).

Embodiment 34:

Preparation of a conjugated compound P32 having phenoxathiin, the reaction is as below:

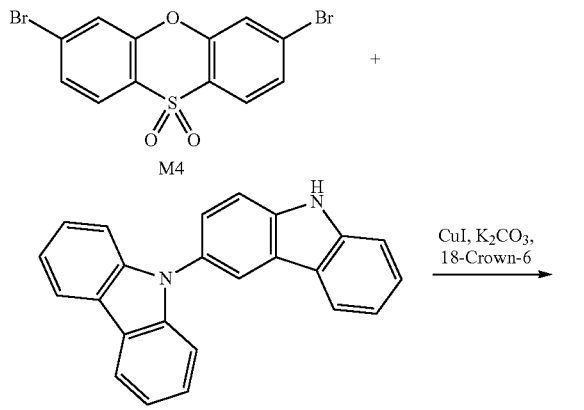

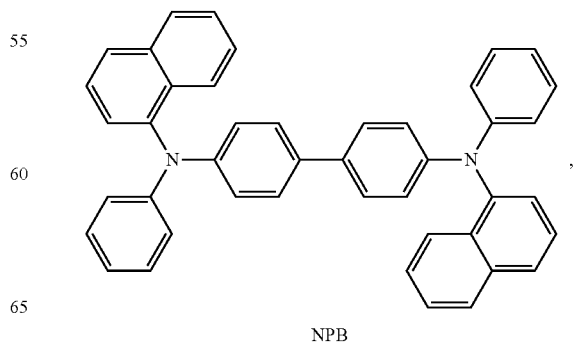

Under nitrogen, M4 (1.28 g, 3.5 mmol), 15 mL of N,N-dimethyl vinyl urea, CuI (0.56 g), potassium carbonate (1.40 g), 9-hydrogen-3-9'-bis carbazole (7.2 mmol, 2.4 g) and 18-crown-6 (0.21 g) are incorporated into a 100 mL flask The reactant is stirred under 160° C. so as to undergo reactions for 24 hours. The solution is extracted by dichloromethane. The organic phase is collected, and then dried by anhydrous magnesium sulfate. Then, a vacuum filtration process is performed. The solvent of the filtered solution is removed by vacuum filtration. After separated by column chromatography, a white product is obtained. After drying, a high purity product is obtained by sublimation under vacuum condition (1.70 g, yield: 55%).

Embodiment 35:

Preparation of OLED Device

The organic light-emitting diode device comprises a substrate, an anode, a hole injection layer, a hole transfer layer, a light emitting layer, an electron transfer layer and a cathode disposed in sequence from the bottom to the top. The substrate is a glass substrate, and the material of the anode is indium tin oxide (ITO). The substrate and the anode form an ITO glass. The ITO glass is washed by ultrasonic wave, and then is treated by oxygen plasma. The sheet resistance of the ITO glass is $10\Omega/cm^2$. The material of the hole injection layer is HAT-CN, the material of the hole transfer layer is NPB and TCTA, the material of the light emitting layer is the compound P3 prepared in Embodiment 5, and the material of the electron transfer layer is TPBI. The cathode is a bilayer composite structure constituted by a LiF layer and an Al layer.

Wherein, NPB indicates N,N'-diphenyl-N,N'-(1-naphthyl)-1,1'-biphenyl-4,4'-diamine, TCTA indicates 4,4',4"-tris(carbazol-9-yl)triphenylamine, and TPBI indicitates 1,3,5-tris (1-phenyl-1-H-benzo[d]imidazol-2)benzene.

The structural formulas of HAT-CN, NPB, TCTA and TPBI are:

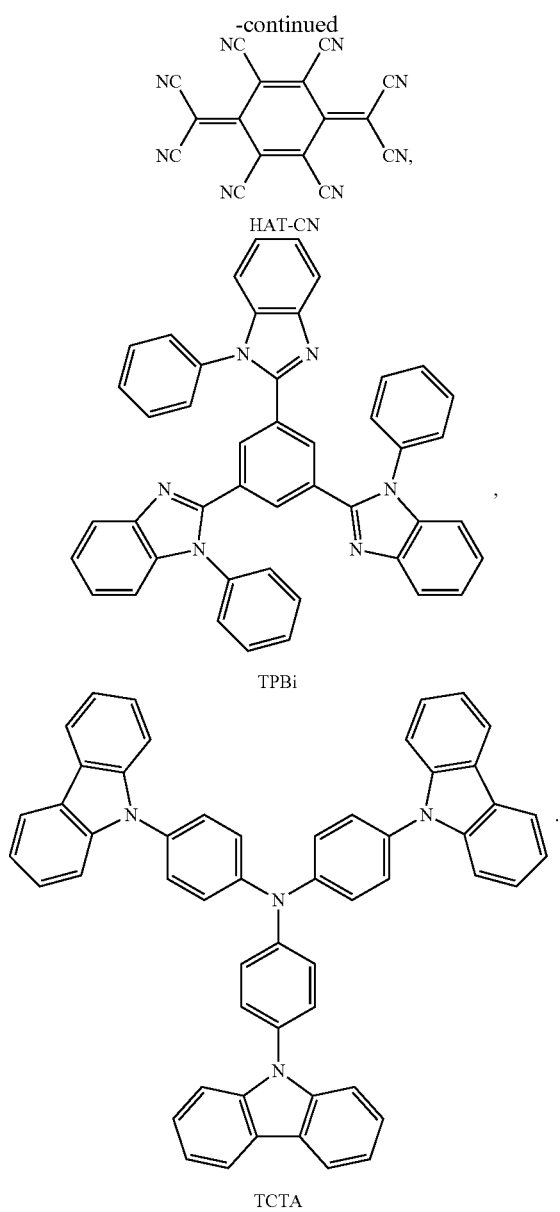

TPBi

TCTA

A positive bias is applied between the anode and the cathode. The device is tested under different currents, and the results are shown in Table 1.

TABLE 1

| The properties of the OLED device when compound P3 is used as the material of light emitting layer | | | | | | | | | | |
|---|---|---|---|---|---|---|---|---|---|---|
| The light emitting material | $V_{on}$ (V) | Maximum efficiency | | Under intensity of 100 cd/m² | | | | Under intensity of 1000 cd/m² | | |
| | | CE (cd/A) | EQE (%) | V (V) | CE (cd/A) | EQE (%) | CIE | V (V) | CE (cd/A) | EQE (%) | CIE |
| P3 | 2.7 | 4.83 | 3.17 | 3.3 | 4.55 | 2.80 | (0.171, 0.208) | 4.4 | 4.76 | 3.13 | (0.156, 0.189) |

Wherein, CE indicates lumen efficiency, EQE indicates external quantum efficiency, and CIE indicates CIE XYZ color space.

Note that the specifications relating to the above embodiments should be construed as exemplary rather than as limitative of the present disclosure. The equivalent variations and modifications on the structures or the process by reference to the specification and the drawings of the disclosure, or application to the other relevant technology fields directly or indirectly should be construed similarly as falling within the protection scope of the disclosure.

What is claimed is:

1. A method for preparing a conjugated compound having phenoxathiin, wherein the method comprises:
   preparing an intermediate having phenoxathiin; and
   reacting the intermediate having phenoxathiin with a compound having an electron-rich conjugated aromatic unit by Suzuki coupling, Buchwald-Hartwig coupling, or Cu-catalyzed amination of halogenated aromatic hydrocarbons for forming the conjugated compound having phenoxathiin,
   wherein the conjugated compound has one of the following formula:

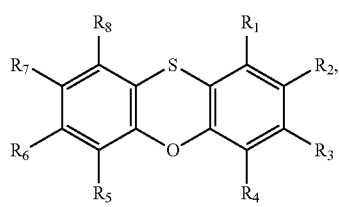

Formula 1

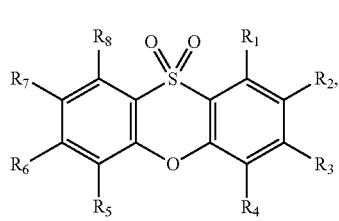

Formula 2 in the Formula 1 and the Formula 2, at least one of $R_1$-$R_8$ is an electron donating group of conjugated aromatic unit, alkyl-substituted aromatic unit, alkoxyl-substituted aromatic unit, alkyl- and alkoxyl-substituted aromatic unit, the aromatic unit is selected from one or more from the group constituted of an aromatic ring formed by vinylene group, ethynylene group, C and H atoms, an aromatic heterocyclic group formed by C, N and H atoms, an aromatic heterocyclic group formed by C, N, O and H atoms, an aromatic heterocyclic group formed by C, S and H atoms, and an aromatic heterocyclic group formed by C, Si and H atoms.

2. The method for preparing the conjugated compound having phenoxathiin according to claim 1, wherein the intermediate having phenoxathiin is compound M1, M2, M3 or M4, and the structural formulas of M1, M2, M3 or M4 are:

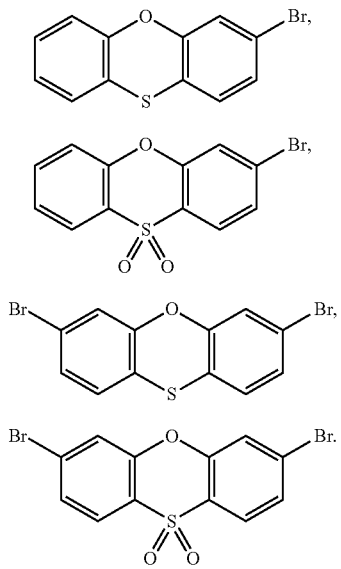

3. The method for preparing the conjugated compound having phenoxathiin according to claim 2, wherein the method and the reactions for preparing the intermediate having phenoxathiin of M1 and M2 are:

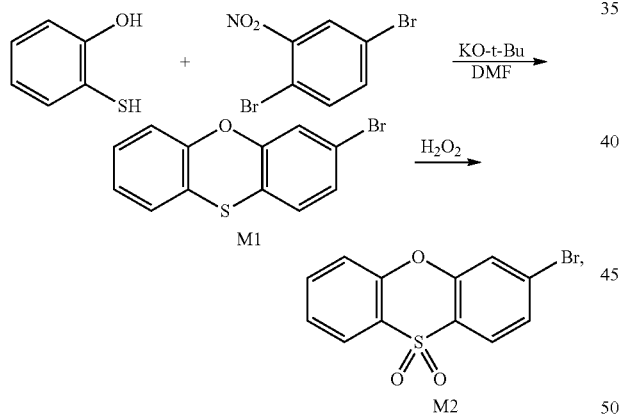

the method for preparing the intermediate having phenoxathiin of M1 is:
3 g of 2-hydroxy-benzenethiol and 120 mL of anhydrous N,N-dimethyl formamide being incorporated into a 250 mL three-necked flask and being stirred under Ar, with the protection of air, 5.47 g of potassium tert-butoxide being incorporated, after stirring for 0.5 hour, 7.01 g of 2,5-dibromo nitrobenzene being slowly incorporated, after stirring for 20 minutes, being heated under reflux overnight, after most of the anhydrous N,N-dimethyl formamide being vaporized by a rotary concentrator, the product being extracted by deionized water and dichloromethane and being separated by silica gel chromatography for obtaining a white solid of the intermediate of M1;

the method for preparing the intermediate having phenoxathiin of M2 is:
4.2 g of M1 and 50 mL of glacial acetic acid being incorporated into a 100 mL three-necked flask, after stirring, 10 mL of 30% hydrogen peroxide being incorporated, then, being heated under reflux overnight, after cooling, alcohol being incorporated, then, being vacuum filtrated, after drying, a white solid of the intermediate of M2 being obtained.

4. The method for preparing the conjugated compound having phenoxathiin according to claim 2, wherein the method and the reactions for preparing the intermediate having phenoxathiin of M3 and M4 are:

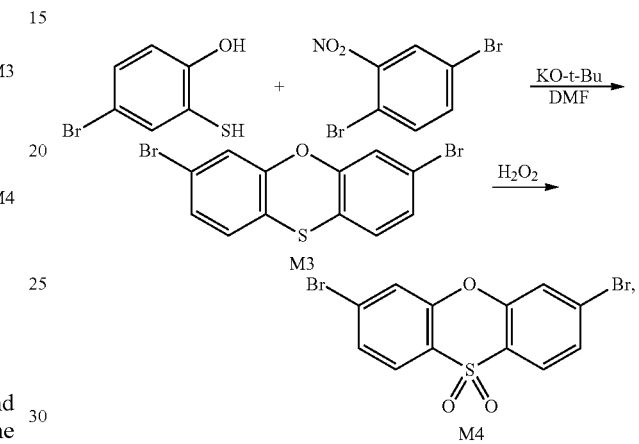

the method for preparing the intermediate having phenoxathiin of M3 is:
5 g of 5-bromo-2-hydroxy-benzenethiol and 120 mL of anhydrous N,N-dimethyl formamide being incorporated into a 250 mL three-necked flask and being stirred under Ar, with the protection of air, 5.47 g of potassium tert-butoxide being slowly incorporated, after stirring for 0.5 hour, 7.01 g of 2,5-dibromo nitrobenzne being incorporated, after stirring for 20 minutes, being heated under reflux overnight, after most of the anhydrous N,N-dimethyl formamide being vaporized by a rotary concentrator, being extracted by deionized water and dichloromethane and being separated by silica gel chromatography for obtaining a white solid of the intermediate of M3; and the method for preparing the intermediate having phenoxathiin of M4 is:
4.6 g of the intermediate of M3 and 50 mL of glacial acetic acid being incorporated into a 100 mL three-necked flask, after stirring, 10 mL of 30% hydrogen peroxide being incorporated, being heated under reflux overnight, after cooling, alcohol being incorporated, being vacuum filtrated, after drying, a white solid of the intermediate of M4 being obtained.

5. The method for preparing the conjugated compound having phenoxathiin according to claim 1, wherein the electron-rich conjugated aromatic unit is N,N-dimethyl vinyl urea, 9,10-dihydro-9,9-dimethyl-acridine, N,N-diphenyl-4-(4,4,5,5-tetramethyl-1,3,2-dioxa pentaborane-2-yl) aniline, bis-(4-tert-butylphenyl) amine, phenothiazine, 9-phenyl-3-(4,4,5,5-tetramethyl-1,3,2-dioxa pentaborane 2-yl) carbazole, phenoxazine or N,N-dimethyl vinyl urea.

6. An organic light-emitting diode device, comprising a substrate, an anode, a hole injection layer, a hole transfer layer, a light emitting layer, an electron transfer layer and a cathode disposed in sequence from the bottom to the top, characterized by, the light emitting layer including a conjugated compound having phenoxathiin,
wherein the conjugated compound has one of the following formula:

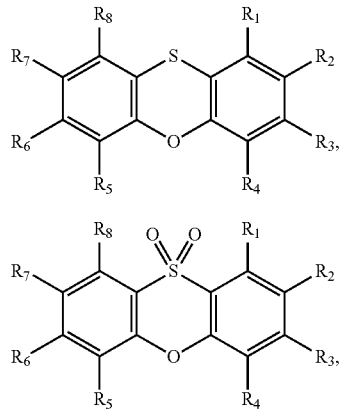

in the Formula 1 and the Formula 2, at least one of $R_1$-$R_8$ is an electron donating group of conjugated aromatic unit, alkyl-substituted aromatic unit, alkoxyl-substituted aromatic unit, alkyl- and alkoxyl-substituted aromatic unit, the aromatic unit is selected from one or more from the group constituted of an aromatic ring formed by vinylene group, ethynylene group, C and H atoms, an aromatic heterocyclic group formed by C, N and H atoms, an aromatic heterocyclic group formed by C, N, O and H atoms, an aromatic heterocyclic group formed by C, S and H atoms, and an aromatic heterocyclic group formed by C, Si and H atoms.

7. The organic light-emitting diode device according to claim 6, wherein the light emitting layer is formed by vacuum vapor deposition or solution coating.

8. The organic light-emitting diode device according to claim 6, wherein the substrate is a glass substrate, the material of the anode is indium tin oxide, and the cathode is a bilayer composite structure constituted by a LiF layer and an Al layer.

9. The organic light-emitting diode device according to claim 6, wherein the material of the hole injection layer is HAT-CN, the material of the hole transfer layer is NPB and TCTA, the material of the electron transfer layer is TPBI, the structural formulas of HAT-CN, NPB, TCTA and TPBI are:

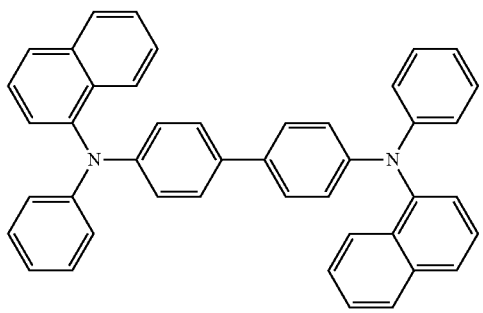
NPB

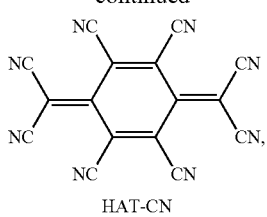
HAT-CN

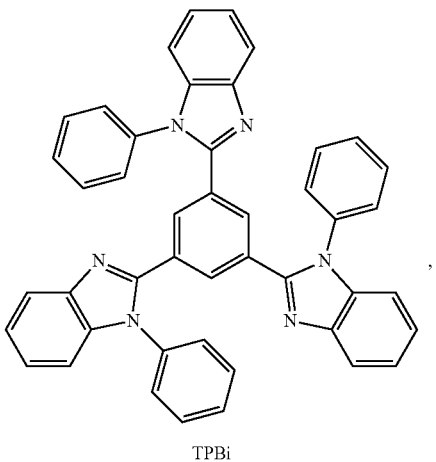
TPBi

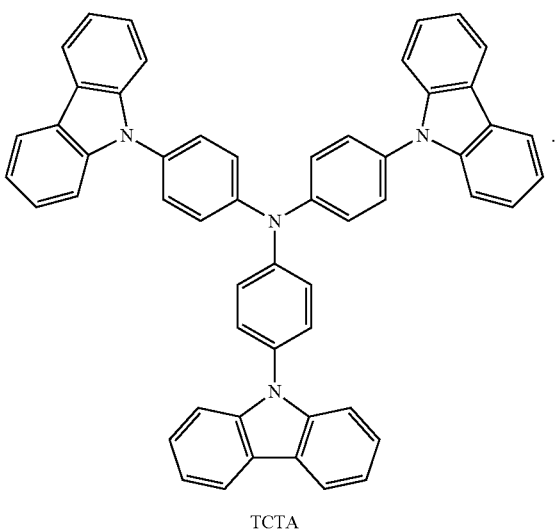
TCTA

* * * * *